United States Patent
Doherty et al.

(10) Patent No.: US 11,531,032 B2
(45) Date of Patent: Dec. 20, 2022

(54) METHODS FOR MEASURING ANALYTE AND/OR PROTEIN IN BIOLOGICAL SAMPLES

(71) Applicant: IDEXX LABORATORIES, INC., Westbrook, ME (US)

(72) Inventors: Patrick Doherty, Biddeford, ME (US); Kevin Kirspel, Cumming, GA (US); Giosi Farace, Georgetown, ME (US); Murthy VSN Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 322 days.

(21) Appl. No.: 16/243,882

(22) Filed: Jan. 9, 2019

(65) Prior Publication Data

US 2019/0219589 A1   Jul. 18, 2019

Related U.S. Application Data

(60) Provisional application No. 62/615,242, filed on Jan. 9, 2018.

(51) Int. Cl.
| | | |
|---|---|---|
| *G01N 33/52* | (2006.01) | |
| *G06T 7/00* | (2017.01) | |
| *H04N 5/235* | (2006.01) | |
| *G01N 33/68* | (2006.01) | |
| *G01N 31/22* | (2006.01) | |

(Continued)

(52) U.S. Cl.
CPC ........... *G01N 33/6827* (2013.01); *G01N 1/30* (2013.01); *G01N 21/272* (2013.01); *G01N 21/78* (2013.01); *G01N 21/82* (2013.01); *G01N 31/22* (2013.01); *G01N 33/52* (2013.01); *G06T 7/0012* (2013.01); *H04N 5/2353* (2013.01); *G06T 2207/10144* (2013.01); *G06T 2207/30242* (2013.01)

(58) Field of Classification Search
CPC .... G01N 33/6827; G01N 33/52; G01N 31/22; G01N 21/78; G01N 21/82; G01N 21/272; G01N 1/30; G06T 7/0012; G06T 2207/10144; G06T 2207/3024; H04N 5/2353

See application file for complete search history.

(56) References Cited

U.S. PATENT DOCUMENTS

| | | |
|---|---|---|
| 4,818,703 A | 4/1989 | Pizzolante |
| 4,950,611 A | 8/1990 | Seaton |

(Continued)

OTHER PUBLICATIONS

Kehoe, Eric, and R. Lee Penn. "Introducing colorimetric analysis with camera phones and digital cameras: an activity for high school or general chemistry." Journal of Chemical Education 90.9 (2013): 1191-1195. (Year: 2013).*

(Continued)

*Primary Examiner* — Vu Le
*Assistant Examiner* — Tracy Mangialaschi
(74) *Attorney, Agent, or Firm* — McDonnell Boehnen Hulbert & Bergthoff LLP

(57) ABSTRACT

The disclosure directed to methods for measuring an analyte alone or in combination with total protein in biological samples. More particularly, the disclosure relates to methods for measuring an analyte and/or total protein using one or more colorimetric reagents alone or in combination with protein precipitation reagents.

30 Claims, 15 Drawing Sheets

(51) Int. Cl.
  *G01N 21/27* (2006.01)
  *G01N 1/30* (2006.01)
  *G01N 21/82* (2006.01)
  *G01N 21/78* (2006.01)

(56) References Cited

U.S. PATENT DOCUMENTS

| | | | |
|---|---|---|---|
| 4,960,710 | A | 10/1990 | Lau |
| 5,087,575 | A | 2/1992 | Lau |
| 5,374,561 | A | 12/1994 | Pugia |
| 5,385,847 | A | 1/1995 | Yip |
| 5,464,777 | A | 11/1995 | Yip |
| 5,527,708 | A | 6/1996 | Blass |
| 5,726,062 | A * | 3/1998 | Numa ............... G01N 33/52 422/410 |
| 6,046,052 | A | 4/2000 | Arter |
| 6,319,721 | B1 | 11/2001 | Kosaka |
| 6,326,605 | B1 | 12/2001 | Modlin |
| 6,797,520 | B2 | 9/2004 | Kosaka |
| 7,745,153 | B2 | 6/2010 | Mallia |
| 8,460,877 | B2 | 6/2013 | Kosaka |
| 2002/0056803 | A1 | 5/2002 | Modlin |
| 2013/0267032 | A1* | 10/2013 | Tsai ............... G06K 9/4652 436/95 |

OTHER PUBLICATIONS

Wang, ShuQi, et al. "Integration of cell phone imaging with microchip ELISA to detect ovarian cancer HE4 biomarker in urine at the point-of-care." Lab on a Chip 11.20 (2011): 3411-3418. (Year: 2011).*

Morais, Camilo LM, et al. "Determination of serum protein content using cell phone image analysis." Analytical Methods 8.34 (2016): 6458-6462. (Year: 2016).*

Alzweiri, Muhammed, et al. "Comparison of different water-miscible solvents for the preparation of plasma and urine samples in metabolic profiling studies." Taianta 74.4 (2008): 1060-1065. (Year: 2008).*

Cmiel, Vratislav, et al. "Smartphone based point-of-care detector of urine albumin." Optical Diagnostics and Sensing XVI: Toward Point-of-Care Diagnostics. vol. 9715. International Society for Optics and Photonics, 2016. (Year: 2016).*

Miura, Kenji. "Imaging and detection technologies for image analysis in electrophoresis." Electrophoresis 22.5 (2001): 801-813. (Year: 2001).*

Velikova, Marina, et al. "Smartphone-based analysis of biochemical tests for health monitoring support at home." Healthcare technology letters 1.3 (2014): 92-97. (Year: 2014).*

The Partial International Search Report for PCT/US2019/012890, 2 pages, dated Apr. 4, 2019.

Battiato et al., "Exposure correction for imaging devices: an overview" Single-Sensor Imaging, Rastislav Lukac (Ed.) Ch 12 (2008).

Benedict et al., "Some applications of a new color reaction for creatinine" J. Biol. Chem. 114:515-532 (1936).

Bonsnes et al., "On the colorimetric determination of creatinine by the Jaffe reaction" J. Biol. Chem. 158:581-591 (1945).

Fujita et al., "Determination of proteins by using the color reaction with pyrocatecol violet-molybdenum (vi) complex" Chem. Pharm. Bull. 32(10): 4161-4164 (1984).

Harley et al., "Proteinuria in dogs and cats" Can. Vet. J. 53: 631-638 (2012).

Kehoe et al., "Introducing colorimetric analysis with camera phones and digital cameras: an activity for high school or general chemistry," J. Chem. Ed. 90(9):1191-1195 (2013).

Kim et al., "Smartphone-based low light detection for bioluminescence application," Scientific Reports 7(1): 40203 (2017).

Langley et al., "The determination of creatinine with sodium 3,5-dinitrobenzoate" J. Biol. Chem. 115:333-341 (1936).

Parekh, et al., "A new method for the determination of serum creatinine based on reaction with 3,5-dinitrobenzoyl chloride in an organic medium" Clin. Chim. Acta 73(2):221-31 (1976).

Parikh et al., "Urine microscopy is associated with severity and worsening of acute kidney injury in hospitalized patients" Clin. J. Am. Nephrol 5(3): 402-408 (2010).

Stookey, "Ferrozine- a new spectrophotometric reagent for iron," Analytical Chemistry 42(7):779-781 (1970).

The International Search Report for PCT/US2019/012890, 6 pages, dated Jun. 18, 2019.

* cited by examiner ered with the concentration of the analyte or the total protein in the sample. In certain embodiments, this method measures the concentration of the analyte. In certain embodiments, this method measures the concentration of the total protein.

METHODS FOR MEASURING ANALYTE AND/OR PROTEIN IN BIOLOGICAL SAMPLES

CROSS REFERENCE TO RELATED APPLICATIONS

This application claims the benefit of priority of U.S. Provisional Patent Application No. 62/615,242, filed Jan. 9, 2018, which is hereby incorporated by reference in its entirety.

FIELD

The disclosure relates generally to methods for measuring an analyte and/or total protein in biological samples. More particularly, the disclosure relates to methods for measuring an analyte and/or total protein using one or more colorimetric reagents alone or in combination with protein precipitation reagents.

BACKGROUND

To screen for a number of health conditions, it is often necessary to analyze biological samples for amounts of one or more analytes, such as red or white blood cells, calcium ions, potassium ions, chloride ions, sodium ions, glucose, lactate, creatinine, creatine, urea, uric acid, ethanol, albumin, alkaline phosphatase, cholesterol, pyruvate, β-hydroxybutyrate, alanine aminotrasferase, aspartate aminotransferase, cetylcholinesterase, etc. In addition to measuring a particular analyte(s), it may also be helpful to measure an amount of total protein present in a sample. For example, measuring total protein may be helpful in the diagnosis of renal disease or acute kidney injury. The analysis of concentrations of a particular analyte(s) and total protein in a biological sample typically require sending the sample to laboratory for analysis. This results in increased sample handling, long turnaround times for laboratory results, special shipping requirements, and increased storage times, which in turn may lead to bacterial contaminations and/or bacterial over growth in the sample, changes in the levels of key proteins, the degradation of casts and cells, the dissolution or formation of crystals, changes in pH of the sample, increased odor of the sample, and other deleterious effects on the sample.

SUMMARY

Accordingly, the inventors have identified a need for a point of care assay that can measure analyte concentrations, total protein content, or combinations thereof in biological and other samples that is efficient, accurate, and cost-effective.

One aspect of the disclosure provides methods of measuring a concentration of an analyte or total protein in a sample. The method includes contacting the sample with a colorimetric reagent to obtain a processed sample. The method further includes focusing a camera including an aperture at the processed sample, opening the aperture for a period of time sufficient to collect a predetermined amount of light from the sample, and measuring the period of time that the aperture is open. The period of time that the aperture is open is then correlated with the concentration of the analyte or the total protein in the sample. In certain embodiments, this method measures the concentration of the analyte. In certain embodiments, this method measures the concentration of the total protein.

In another aspect of the methods of measuring a concentration of an analyte or total protein in a sample of the disclosure, the method includes contacting the sample with a colorimetric reagent to obtain a processed sample. The method further includes focusing a camera including an aperture at the processed sample; opening the aperture for a predetermined period of time, wherein the size of the aperture is sufficient to collect a predetermined amount of light from the sample; and measuring the size of the aperture. The size of the aperture is then correlated to the concentration of the analyte or the total protein in the sample. In certain embodiments, this method measures the concentration of the analyte. In certain embodiments, this method measures the concentration of the total protein.

One aspect of the disclosure provides methods of measuring a concentration of total protein in a sample. The method includes contacting the sample with a protein precipitation reagent to obtain a processed sample including a protein precipitate. The method further includes generating an image of the processed sample by a camera, and measuring a number of pixels that correlates to the protein precipitate in the image. The number of pixels is then correlated to a standard curve to obtain the concentration of total protein in the sample.

Another aspect of the disclosure provides methods of measuring a concentration of an analyte and total protein in a sample. The method includes contacting the sample with a colorimetric reagent and a protein precipitation reagent to obtain a processed sample including a protein precipitate. The method further includes determining the concentration of the analyte in the processed sample by focusing a camera including an aperture at the processed sample; opening the aperture for a period of time sufficient to collect a predetermined amount of light from the processed sample; measuring the period of time that the aperture is open; and correlating the period of time that the aperture is open with the concentration of the analyte in the sample. The method further includes determining the concentration of total protein by generating an image of the processed sample by a camera; measuring a number of pixels that correlates to the protein precipitate in the image; and correlating the number of pixels with a standard curve to obtain the concentration of total protein in the sample.

In another aspect of the methods of measuring a concentration of an analyte and total protein in a sample of the disclosure, the method includes contacting the sample with a colorimetric reagent and a protein precipitation reagent to obtain a processed sample including a protein precipitate. The method further includes determining a concentration of an analyte in the processed sample by focusing a camera including an aperture at the processed sample; opening the aperture for a predetermined period of time, wherein the size of the aperture is sufficient to collect a predetermined amount of light from the sample; measuring the size of the aperture; and correlating the size of the aperture with the concentration of the analyte in the sample. The method further includes determining the concentration of total protein by generating an image of the processed sample by a camera; measuring a number of pixels that correlates to the protein precipitate in the image; and correlating the number of pixels with a standard curve to obtain the concentration of total protein in the sample.

In another aspect of the methods of measuring a concentration of an analyte and total protein in a sample of the disclosure, the method includes contacting the sample with a colorimetric reagent and a protein precipitation reagent to obtain a processed sample including a protein precipitate. The method further includes determining a concentration of an analyte in the processed sample by focusing a camera at the processed sample; opening the aperture to collect an amount of light from the sample; measuring an intensity of the collected amount of light; and correlating the intensity of the collected light with the concentration of the analyte in the sample. The method further includes determining the concentration of total protein by generating an image of the processed sample by a camera; measuring a number of pixels that correlates to the protein precipitate in the image; and correlating the number of pixels with a standard curve to obtain the concentration of total protein in the sample.

In certain embodiments of the methods of the disclosure, the analyte may be selected from calcium ion, potassium ion, chloride ion, sodium ion, glucose, lactate, creatinine, creatine, urea, uric acid, ethanol, albumin, alkaline phosphatase, cholesterol, pyruvate, β-hydroxybutyrate, alanine aminotrasferase, aspartate aminotransferase, and cetylcholinesterase. In certain embodiments of the methods of the disclosure, the analyte may be creatinine, glucose, albumin, or alkaline phosphatase.

In certain embodiments of the methods of the disclosure, the colorimetric reagent may be 2,4,6-trinitrophenol and a base. In certain embodiments of the methods of the disclosure, the colorimetric reagent is methyl 3,5-dinitrobenzoate, 3,5-dinitrobenzoic acid, or 3,5-dinitrobenzoylchloride, and a base or a basic buffer. In certain embodiments of the methods of the disclosure, the colorimetric reagent is a reagent system comprising cupric ions, a hydroperoxide, and an oxidizable dye. In certain embodiments of the methods of the disclosure, the colorimetric reagent comprises 3,5-dinitrobenzoylchloride. In certain embodiments of the methods of the disclosure, the colorimetric reagent may be one or more of glucose oxidase, hexokinase, alkaline copper tartarate, alkaline ferricyanide, and horseradish peroxidase. In certain embodiments of the methods of the disclosure, the colorimetric reagent may be bromocresol green. In certain embodiments of the methods of the disclosure, the colorimetric reagent may be a reagent system comprising 5-bromo-4-chloro-3-indolyl phosphate (BCIP) and nitro blue tetrazolium (NBT). In certain embodiments of the methods of the disclosure, the colorimetric reagent may comprise pyrocatechol violet, benzethonium chloride, or pyrogallol red. In certain embodiments of the methods of the disclosure, the colorimetric reagent may comprise pyrocatechol violet.

In certain embodiments of the methods of the disclosure, the colorimetric reagent may include one or more reagents suitable for an immunoassay. For example, the colorimetric reagent may include one or more analyte-specific antibodies and/or enzymes suitable for enzyme-linked immunosorbent assay (ELISA) or enzyme multiplied immunoassay technique (EIMT).

In certain embodiments of the methods of the disclosure, the protein precipitation reagent may be one or more water-miscible solvents (such as alcohol, e.g., isopropanol, methanol, or ethanol, ketone, e.g., acetone, methyl ethyl ketone, methyl isobutyl ketone, or cyclohexanone, tetrahydrofuran); or the protein precipitation reagent is a salt (such as ammonium sulfate or salts comprising polyvalent metallic ions); or the protein precipitation reagent is trichloroacetic acid, or trichloroacetic acid and acetone; or the protein precipitation reagent is a polymer (e.g., a non-ionic hydrophilic polymer, such as polyethylene glycols and dextrans). In certain embodiments of the methods of the disclosure, the protein precipitation reagent may be an aqueous surfactant. In certain embodiments of the methods of the disclosure, the aqueous surfactant may be benzalkonium chloride or benzethonium chloride.

In certain embodiments of the methods of the disclosure, the sample may be a urine sample.

In certain embodiments, the methods of the disclosure may further comprise generating an image of the processed sample using the predetermined amount of light collected from the processed sample. In certain embodiments of the methods of the disclosure, the processed sample may be imaged from a slide comprising the processed sample. In certain embodiments of the methods of the disclosure, the image may be a black and white image.

In certain embodiments, the methods of the disclosure may further comprise displaying the image of the processed sample on a user interface. In certain embodiments of the methods of the disclosure, the predetermined amount of light may be sufficient to measure an amount of the protein precipitate from an image of the processed sample. In certain embodiments of the methods of the disclosure, the predetermined amount of light may be constant. In certain embodiments of the methods of the disclosure, the predetermined amount of light may be selected by a user of the camera. In certain embodiments of the methods of the disclosure, the camera may comprise a filter. In certain embodiments of the methods of the disclosure, the filter may be configured to pass wavelengths corresponding to a wavelength range of the color resulting from the reaction between the colorimetric reagent and the sample. In certain embodiments of the methods of the disclosure, the camera may comprise an automatic exposure function, and wherein measuring the period of time that the aperture is open comprises determining the period of time using the automatic exposure function. In certain embodiments of the methods of the disclosure, the determination may be made based on at least one of the aperture size and the predetermined amount of light.

In certain embodiments of the methods of the disclosure, the camera may comprise a sensor, and wherein opening the aperture for a period of time sufficient to collect a predetermined amount of light from the sample comprises: opening the aperture; detecting by the sensor an amount of light collected by the camera; determining whether the amount of light collected by the camera is substantially equivalent to the predetermined amount of light; and closing the aperture after determining that the predetermined amount of light has been collected by the camera.

In certain embodiments of the methods of the disclosure, the camera may comprise a sensor, and wherein opening the aperture for a period of time sufficient to collect a predetermined amount of light from the sample comprises: opening the aperture for a period of time to collect an amount of light from the processed sample; closing the aperture; measuring the amount of light collected from the processed sample by the sensor; determining whether the amount of light collected from the processed sample is substantially equivalent to the predetermined amount of light; opening the aperture for a second period of time if the amount of light received from the sample is not substantially equivalent to the predetermined amount of light, wherein the second period of time is different than the first period of time; and correlating the second period of time that the aperture is open with the predetermined amount of light to obtain the concentration of the analyte or the total protein in the sample.

In certain embodiments of the methods of the disclosure, the camera may comprise an automatic exposure function, and wherein measuring the size of the aperture comprises determining the size of the aperture using the automatic exposure function. In certain embodiments of the methods of the disclosure, the determination may be made based on at least one of the period of time and the predetermined amount of light.

In certain embodiments of the methods of the disclosure, the camera may comprise a sensor, and wherein opening the aperture for a period of time comprises: opening the aperture to collect an amount of light from the sample, wherein the aperture comprises a first aperture size; closing the aperture; measuring the amount of light collected from the processed sample by the sensor; determining whether the amount of light collected from the sample is substantially equivalent to the predetermined amount of light; opening the aperture for a second period of time if the amount of light received from the sample is not substantially equivalent to the predetermined amount of light, wherein the aperture has a second aperture size, wherein the second aperture size is different than the first aperture size; and correlating the second aperture size of the aperture with the predetermined amount of light to obtain the concentration of the analyte or the total protein in the sample. In certain embodiments, the methods of the disclosure may further comprise determining a protein: creatinine ratio of the sample based on at least the concentration of creatinine in the sample and the concentration of total protein in the sample.

In certain embodiments, the methods of the disclosure may further comprise making a health determination based on at least the concentration of the analyte and/or the total protein in the sample.

The foregoing summary is illustrative only and is not intended to be in any way limiting. In addition to the illustrative aspects, embodiments, and features described above, further aspects, embodiments, and features will become apparent by reference to the figures and the following detailed description.

DESCRIPTION

Figure 1:
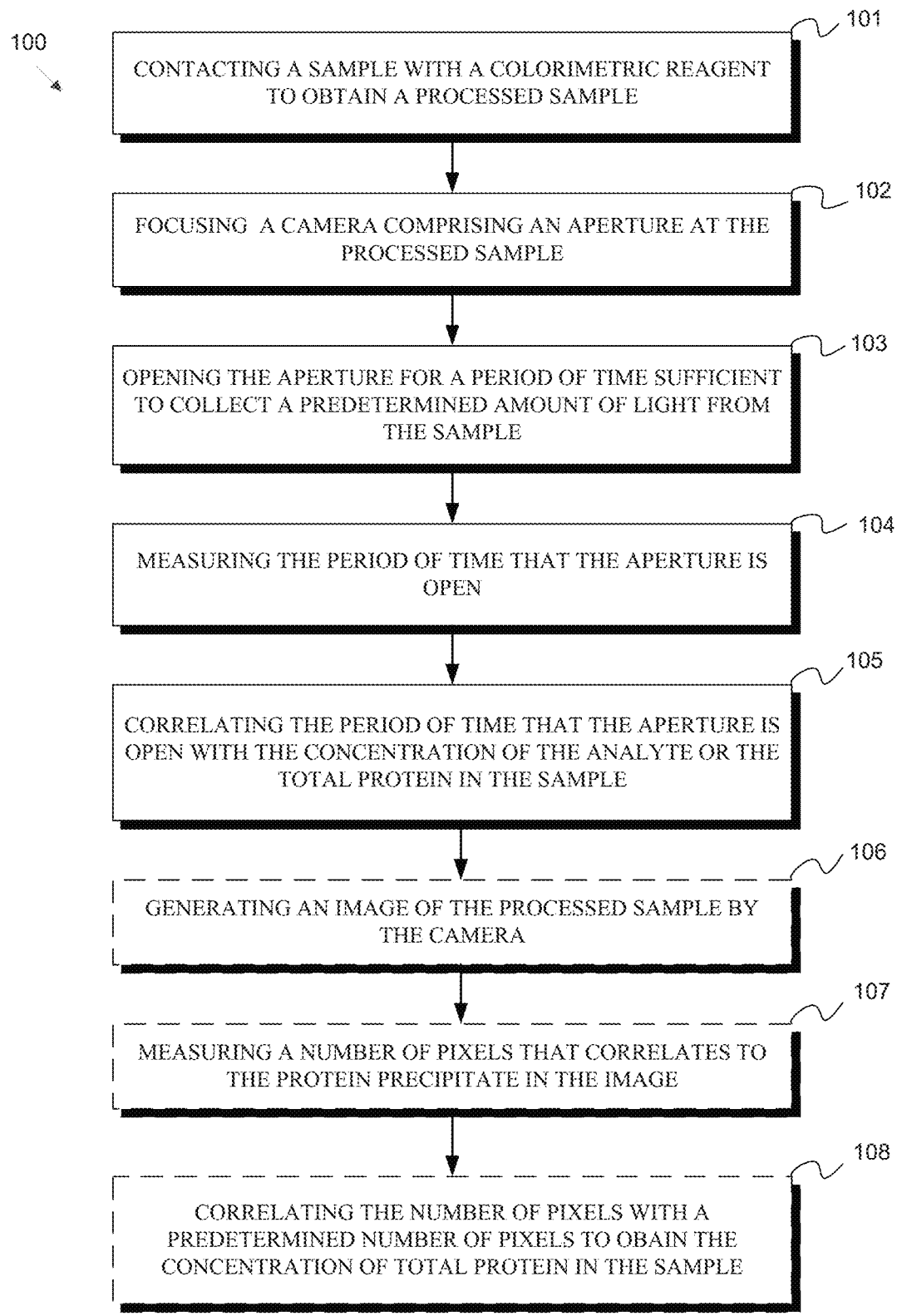
FIG. 1 is a flowchart of a method according to one embodiment of the disclosure.

In general, the disclosed materials, methods, and apparatus provide improvements for measuring concentrations of analytes and/or total protein in a biological sample. Specifically, in certain embodiments of the disclosure, an analyte and/or total protein in a biological sample are measured using a single sample, a single image, and/or a single assay that eliminate multiple test methods, extensive sample handling, shipping and storage. The measurements can be timely performed in-clinic that can result in fewer changes to the sample compared to traditional methods. For example, compared to samples analyzed according to traditional methods, the samples analyzed according to the methods of the disclosure may have less bacterial contaminations and/or bacterial over growth, minimal or no changes in the levels of key proteins, less degradation of casts and cells, less dissolution or formation of crystals, and minimal or no changes in pH, appearance, and/or odor.

The term "biological sample," as used herein, generally refers to a sample of tissue or fluid from a human or animal including, but not limited to whole blood, plasma, serum, spinal fluid such as cerebral-spinal fluid; lymph fluid, abdominal fluid (ascites), the external sections of skin, respiratory, intestinal and genitourinary tracts, tears, saliva, urine, blood cells, tumors, organs, tissue, and sample of in vitro cell culture constituents.

As used herein, the term "total protein" refers to all proteins in a sample, including protein fragments of any size.

In various aspects of the methods of the disclosure, the sample volume is between about 10 µL and about 500 µL; for example, from about 10 µL to about 300 µL, or about 10 µL to about 200 µL, or about 10 µL to about 100 µL, or about 50 µL to about 300 µL, or about 50 µL to about 200 µL, or about 100 µL to about 500 µL, or about 100 µL to about 300 µL, or about 100 µL to about 200 µL. In some aspects, the method of the disclosure requires less sample volume than traditional methods for measuring analytes, total protein and combinations thereof.

The methods of the disclosure include creating a processed sample by contacting a biological sample with a colorimetric reagent for determining an analyte and/or a colorimetric or protein precipitating reagent to determine total protein. Depending on the concentration of the analyte and/or the total protein in the sample, the reaction between the colorimetric reagent(s) and the analyte and/or the total protein may cause the solution to change color to a varying degree. A camera may be used to take an image of the processed sample by collecting an amount of light from the sample through an aperture of the camera, wherein the amount of light that is collected is indicative of the color of the sample.

In certain embodiments, the camera collects (or a sensor associated with the camera collects) a predetermined amount of light regardless of the color of the sample. The amount of predetermined light that is collected may be determined experimentally, for instance by one, two, three, or more empirical experiments to obtain a value or values for a predetermined amount of light that correlates to a concentration or concentrations of the analyte or the total protein in the sample. The predetermined amount of light should not be more that the maximum amount of light or less than the minimum amount of light that the camera can accept.

The amount of light collected by the cameral may be dependent on the exposure time, aperture size and other features of the camera. For example, the predetermined amount of light from a sample containing albumin at a concentration of 1 mg/mL obtained using a PL-D725MU-T USB 3.0 camera (PixelLINK) with a CMOS light sensor and an objective lens with a magnification of 10× and a numerical aperture of 0.28 may be collected with an exposure time of about 170 ms to about 180 ms. This time represents an amount of time that the aperture of the camera is open in order to collect the light on a sensor of other light collection device. Therefore, a predetermined amount of light may be defined by the exposure time or shutter speed of the camera instead of a value directly representing the amount of light (e.g., photons).

In another example, the predetermined amount of light from a sample containing glucose at a concentration of 1 mM obtained using a PL-D725MU-T USB 3.0 camera (PixelLINK) with a CMOS light sensor and an objective lens with a magnification of 10× and a numerical aperture of 0.28 may be collected with an exposure time of about 130 ms and 140 ms. In another example, the predetermined amount of light for a sample containing alkaline phosphatase at a concentration of 1 µg/mL obtained using a PL-D725MU-T USB 3.0 camera described above may be collected with an exposure time in the range of about 135 ms and about 145 ms.

By collecting a predetermined (i.e., a discrete) amount of light from each sample, the camera can produce an image or plurality of images that have substantially the same exposure or brightness, no matter the color of the sample. Accordingly, camera settings (e.g., the shutter speed and/or aperture size) may be varied image-to-image in order to achieve the predetermined level of exposure in each image of the processed samples. These camera settings may be measured to indicate an optical property of the processed sample (e.g., the colorimetric intensity of the processed sample). For example, if the aperture size is held constant, the shutter speed required to reach the desired exposure level may vary depending on the colorimetric intensity of the processed sample. The shutter speed may then be measured and correlated to the concentration of an analyte and/or total protein in the sample. Conversely, if the shutter speed is held constant, the aperture size required to reach the predetermined exposure level can be measured and may be correlated to the concentration of an analyte and/or the total protein in the sample. By generating an image that has a predetermined level of exposure, the camera may be configured to produce clinically useful images of the sample no matter the colorimetric intensity of the processed sample. In certain embodiments, the method may be used to measure the concentration of the analyte and/or the concentration of the total protein, wherein the concentration of the analyte is determined with a first colorimetric reagent and the concentration of the total protein may be determined with a second colorimetric reagent.

Accordingly, a method of the disclosure includes contacting the sample with a colorimetric reagent to obtain a processed sample; focusing a camera comprising an aperture at the processed sample; opening the aperture for a period of time sufficient to collect a predetermined amount of light from the sample; measuring the period of time; and correlating the period of time with the concentration of the analyte or the total protein in the sample. Another method of the disclosure includes contacting the sample with a colorimetric reagent to obtain a processed sample; focusing a camera comprising an aperture at the processed sample; opening the aperture for a predetermined period of time, wherein the size of the aperture is sufficient to collect a predetermined amount of light from the sample during the predetermined time; measuring the size of the aperture; and correlating the size of the aperture with the concentration of the analyte or the total protein in the sample. Correlating the period of time or size of the aperture with the concentration of analyte or total protein can be accomplished by comparing the time or the aperture size to a standard curve. The standard curve can represent the amount an amount of time or the size of the aperture of the camera for a series of concentrations of analyte or total protein in the sample.

In addition to or as an alternative to measuring a concentration of an analyte or protein as a result of the color intensity of the sample, the methods of the disclosure includes the measurement of the concentration of total protein in the sample by contacting the sample with a protein precipitation reagent to obtain a processed sample including a protein precipitate. The protein precipitate may be visible following the reaction with the protein precipitation reagent. The total protein concentration may be measured by generating an image of the processed sample by a camera and analyzing such image. The image analysis may include, for instance, measuring a number of pixels that correlates to the protein precipitate (e.g., to protein precipitate globules or an area of the image that consists of a protein precipitate). The number of pixels may be then compared to a standard curve reflecting a correlation between pixels and protein concentration to obtain the concentration of total protein in the sample. This test method may be performed more quickly than traditional tests, allow for greater dynamic range, decrease the cost of analysis, and/or use fewer reagents and materials. In some embodiments of the disclosure, the total protein is measured, using the camera image, without the measurement of another analyte.

The methods of the disclosure may be used to measure concentrations of numerous analytes including but not limited to one or more of the following compounds that may be present in biological samples: calcium ion, potassium ion, chloride ion, sodium ion, glucose, lactate, creatinine, creatine, urea, uric acid, ethanol, albumin, alkaline phosphatase, cholesterol, pyruvate, β-hydroxybutyrate, alanine aminotrasferase, aspartate aminotransferase, and cetylcholinesterase. In some embodiments, the analyte may be selected from one or more of creatinine, glucose, albumin, and alkaline phosphatase.

As noted above, the methods of the disclosure include contacting a sample with a colorimetric reagent to obtain a processed sample as represented by step 101 of the method 100 in the flow chart of FIG. 1. Colorimetric reagents may be selected based on the desired applications and types of analyte to be measured. For example, colorimetric reagents for measuring creatinine include, but are not limited to, one or more of (1) 2,4,6-trinitrophenol and a base of basic buffer, (2) methyl 3,5-dinitrobenzoate, 3,5-dinitrobenzoic acid, or 3,5-dinitrobenzoylchloride, and a base or a basic buffer, and (3) a reagent system including cupric ions, a hydroperoxide, and an oxidizable dye. For example, colorimetric reagents for measuring glucose include, but are not limited to, one or more of glucose oxidase, hexokinase, alkaline copper tartarate, alkaline ferricyanide, and horseradish peroxidase. For example, colorimetric reagents for measuring albumin include, but are not limited to, bromocresol green. For example, colorimetric reagents for measuring alkaline phosphatase include, but are not limited to, 5-bromo-4-chloro-3-indolyl phosphate (BCIP) and nitro blue tetrazolium (NBT) system. For example, colorimetric reagents for measuring total protein include, but are not limited to, pyrocatechol violet, benzethonium chloride, and pyrogallol red. In certain embodiments of the methods of the disclosure, the colorimetric reagent may include one or more reagents suitable for an immunoassay. For example, the colorimetric reagent may include one or more analyte-specific antibodies and/or enzymes suitable for enzyme-linked immunosorbent assay (ELISA) or enzyme multiplied immunoassay technique (EIMT).

In certain embodiments of the disclosure, the calorimetric reagent may include two or more components (such as, for example, a base or basic buffer in addition to 2,4,6-trinitrophenol). Such components, in certain embodiments, may be added to the sample separately and sequentially. For example, the sample may be first contacted with the base, followed by contacting with 2,4,6-trinitrophenol. In certain embodiments, the components of the calorimetric reagent may be contacted with the sample simultaneously. For example, 3,5-dinitrobenzoic acid or 3,5-dinitrobenzoylchloride may be dissolved into a basic buffer prior to contacting the sample.

The colorimetric reagent used in the methods of the disclosure may be added in a particular volume based on the desired applications and types of analyte to be measured. For example, the colorimetric reagent volume is between about 1 μL and about 500 μL; for example, from about 1 μL to about 300 μL, or about 1 μL to about 200 μL, or about 1 μL to about 100 μL, or about 1 μL to about 50 μL, or about 50 μL to about 300 μL, or about 50 μL to about 200 μL, or about 100 μL to about 500 μL, or about 100 μL to about 300 μL, or about 100 μL to about 200 μL.

Protein precipitation reagents for use in the methods of the disclosure may be selected based on the desired applications and also based on types of analyte to be measured in samples that are also analysed for protein concentrations (for example, the protein precipitation agent may be selected as to reduce interference between this reagent and the reaction of the analyte and colorimetric reagent). For example, protein precipitation reagents include, but are not limited to, one or more of water-miscible solvents (such as alcohol, e.g., isopropanol, methanol, or ethanol, ketone, e.g., acetone, methyl ethyl ketone, methyl isobutyl ketone, or cyclohexanone, tetrahydrofuran), salts (such as ammonium sulfate or salts including polyvalent metallic ions), trichloroacetic acid (alone or in combination with acetone), polymers (e.g., a non-ionic hydrophilic polymer, such as polyethylene glycols and dextrans), aqueous surfactants, benzalkonium chloride, benzethonium chloride, and any combination thereof.

The protein precipitation reagents may be added in a particular volume based on the desired applications. For example, in certain embodiments of the methods of the disclosure, the volume of the protein precipitation reagent is between about 1 μL and about 500 μL; for example, from about 1 μL to about 300 μL, or about 1 μL to about 200 μL, or about 1 μL to about 100 μL, or about 1 μL to about 50 μL, or about 50 μL to about 300 μL, or about 50 μL to about 200 μL, or about 100 μL to about 500 μL, or about 100 μL to about 300 μL, or about 100 μL to about 200 μL.

As noted above, the methods of the disclosure include focusing a camera including an aperture at the processed sample as represented by step 102 of method 100 shown in FIG. 1. The camera may be any device having an aperture that, when open, can collect a light from a processed sample (i.e., to take an image of the sample). The camera may include a variety of imaging systems. In certain embodiments, the camera may include a benchtop imaging platform configured to image a biological sample suspended in a cartridge or slide. In a particular embodiment, the camera may be associated with a urine or blood sediment analyzer, for example, the SEDIVUE™ DX™ Urine Sediment Analyzer (IDEXX Laboratories, Inc., Westbrook, Me.). In such embodiments, the processed sample may be pipetted or otherwise dispensed directly into a cartridge disposed in an entrance port of the system. In other embodiments, the processed sample may be imaged from a slide including the processed sample, and the method may include inserting a slide, cartridge, or another container including the processed sample into an entrance port of the imaging system.

In certain other embodiments, the camera may be a digital camera, a camera phone, or another portable device, and focusing the camera at the processed sample may include positioning the camera to face the sample. In cases where a portable device is used, a stand, tripod, armature, or other support may be configured to position the camera at a particular location relative to the processed sample to image (i.e., collect a predetermined amount of light from) the sample. Focusing such a camera may include manually controlling the focus via a user interface of the camera such that the processed sample is within the focus range of the camera. Additionally or alternatively, focusing the camera may include using an automatic focus function of the camera to focus on the processed sample. Such an automatic focus function of the camera may use a sensor to detect a distance between the processed sample and the camera, and adjust the focus of the camera such that the processed sample is within a focus range of the camera.

Figure 2:
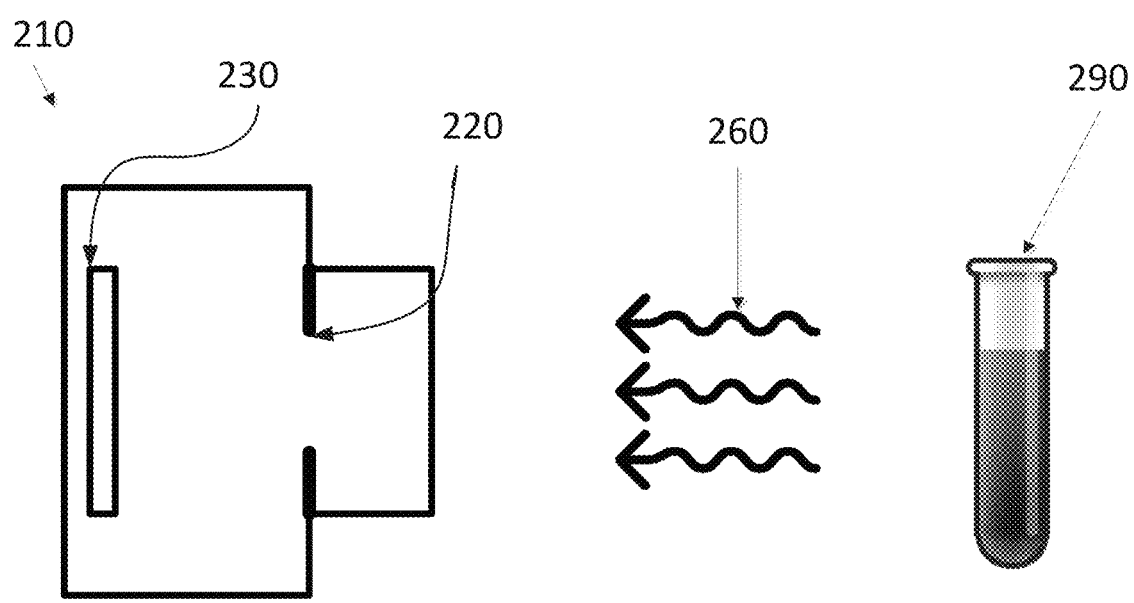
FIG. 2 is a partial schematic of a camera opening an aperture to collect light from a sample, according to an embodiment of the disclosure.

As noted above, the methods of the disclosure include opening the aperture for a period of time sufficient to collect a predetermined amount of light from the sample as represented by step 103 of method 100 in FIG. 1. FIG. 2 further illustrates a simplified schematic of an example camera 210 featuring an aperture 220 and a light sensor 230 for receiving light 260 from a sample 290. When the aperture 220 is open, light 260 from the sample 290 may enter the camera 210, thereby contacting the light sensor 230. The light contacting the sensor may be used to analyze visual characteristics of the sample 290, to produce an image of the sample, or to perform some other type of processing.

The aperture 220 may include any opening through which the camera 210 can collect light 260 for a period of time to determine a color or light intensity of the sample or to generate an image of the prepared sample 290. For example, the aperture 220 may include a shutter of the camera 210, which exposes the light sensor 230 to the light 360 from the sample 290 for a period of time (i.e., a time corresponding to a shutter speed). The size of the aperture 220 may be fixed e.g., set by a manufacturer of the camera 210, such that it is substantially the same each time the aperture is opened. For example, the numerical aperture 220 may be in the range of about 0.025 and about 0.5, or about 0.03 and about 0.5, or about 0.025 and about 0.25, or about 0.03 and about 0.25, or about 0.03 and about 0.5, or about 0.05 and about 0.25, or about 0.05 and about 0.5, or about 0.1 and about 0.25, or about 0.1 and about 0.5.

In embodiments of the disclosure where the aperture size is constant, the amount of light 260 collected by the camera 210 through the aperture 220 may be dependent primarily on the period of time that the aperture is open. In an alternative embodiment, the size of the aperture 220 may be adjustable to allow for a higher or lower flow rate of light 260 into the camera 210 via the aperture, and opening the aperture may include selecting or determining a size of the aperture. An aperture size may be selected manually by a user of the camera 210, e.g., through a user interface of the camera. Alternatively, the aperture size may be determined by the camera 210 by an automatic exposure ("auto exposure") function of the camera.

Opening the aperture 220 for a period of time sufficient to collect a predetermined amount of light 260 may allow the camera to take an image of the sample. The method may include generating an image of the prepared sample 290 using an amount, such as a predetermined amount, of light collected from the processed sample. The image generated by the camera 210 may include a full-color image, a black and white image, or any other image suitable for measurement of an analyte and/or protein in the processed sample. Alternatively, an image may be produced digitally by a light sensor 230, such as a charge-coupled device (CCD), an active pixel sensor (APS), a complementary metal-oxide semiconductor (CMOS), a Foveon X3 sensor, or another sensor. In such an embodiment, the method may include detecting the collected light 260 on a light sensor 230 and/or converting the incident light to an electrical signal. In some examples, such a light sensor 230 may detect the incident light 260 and record it as a series of pixels, representing discrete points on the prepared sample being imaged. Such pixels may be selectively sensitive to light of a particular wavelength or range of wavelengths. For instance, the pixels may be subdivided into pixels which selectively collect light of wavelengths corresponding to the colors green, red, and blue, respectively. Alternatively, such pixels may be sensitive to all collected light in the range of wavelengths to which the sensor is sensitive (i.e., to produce a black and white image). The light sensor 230 may measure the wavelength and/or amount of light collected by each pixel the camera 210 and store it as an array of values in a memory or data storage of the camera. In a particular example, each pixel may comprise a numerical value corresponding to an amount of collected light 260, a mean intensity, brightness, coloration, or another property of the incident light at the pixel. The method may further include displaying the image of the processed sample on a user interface in communication with the camera. Additionally or alternatively, the image and/or associated information may be sent to a remote computing device such as a server, a cell phone, a computer, or another external device.

As described herein, the predetermined amount of light represents an amount of light collected by the camera to produce an image with a predetermined brightness or exposure. The predetermined amount of light may be specified according to an amount of incident light on a light sensor of the camera, a voltage produced by converting the incident light to an electrical signal, a brightness or optical property of a produced image, or by some other means. The predetermined amount of light 260 to be collected by the camera 210 may be constant such that an image of uniform exposure and/or brightness is produced each time the aperture 220 is opened. The predetermined amount of light 260 may be influenced by various elements of the camera or imaging system. For instance, the predetermined amount of light may be related to a lens, aperture, light sensor, or other elements of the camera. The predetermined amount of light 260 may be selected based on an amount of light required to produce a clinically useful image of the processed sample 290.

In embodiments where the amount of a protein precipitate is measured, the predetermined amount of light 260 may be sufficient to measure an amount of a protein precipitate from an image of the processed sample (e.g., by visual inspection of an image of the processed sample), by counting a number of pixels that correlates to the protein precipitate (e.g., to protein precipitate globules or an area of the image that consists of a protein precipitate), and/or by processing the image using a program, algorithm, or some other means. In another embodiment, the predetermined amount of light 260 may be determined based on a desired level of exposure, brightness, contrast, or intensity in an image generated by the camera 210 based on a brightness histogram of an image of the processed sample 290.

The predetermined amount of light 260 may be selected by a user of the camera 210 through a user interface of the camera 210, and the method may include inputting a predetermined amount of light. The predetermined amount of light 260 may be selected or adjusted by a user to ensure clarity of the image and/or to facilitate post-processing of the image. Additionally or alternatively, an optimal or otherwise clinically useful exposure level may be determined using an automatic exposure ("auto exposure") function of the camera 210. Such an auto exposure function may use an algorithm which uses information about the prepared sample 290 and/or the settings of the camera 210 to determine the amount of light 260 the camera should collect to produce a clinically useful image. The predetermined amount of light 260, for instance, may be determined based on an average brightness of the prepared sample 290, a brightness histogram of the prepared sample, identification and/or balancing of highlights and lowlights of the prepared sample, or some other method.

For a given sample, the amount of light 260 collected by the camera 210 through the aperture 220 (i.e., the exposure level of an image produced by the camera) is generally influenced by two camera settings: the size of the aperture 220 and the period of time that the aperture is open. Depending on the optical properties of the processed sample 290, a larger or smaller aperture size and/or a longer or shorter opening of the aperture 220 may be required to collect a predetermined amount of light from the sample. For example, if one sample is darker than another, it will require a larger aperture size and/or a longer shutter speed to collect the same amount of light 260 compared to a lighter sample.

In one embodiment, the methods of the disclosure include measuring the period of time the aperture is open in order to collect the predetermined amount of light as represented by step 104 of the method 100 in FIG. 1. In some embodiments, an auto exposure function of the camera may be used to determine various camera settings before generating an image of the processed sample. In a similar manner that an automatic exposure function can use the optical properties of the sample to determine an optimal exposure level, an auto exposure function may also be used to determine the appropriate camera settings to achieve a predetermined exposure level. In some embodiments, the auto exposure function uses a light sensor of the camera to evaluate the optical properties of the processed sample and determine an appropriate shutter speed of the camera before opening the aperture. The auto exposure function may also use information relating to the predetermined amount of light and/or the aperture size in determining the period of time that the aperture should be opened.

In another embodiment of the disclosure, the camera may include a sensor that measures the collected light in real-time such that the camera can actively respond by closing the aperture when the predetermined amount of light has been collected. Accordingly, such an embodiment may include: (i) opening the aperture; (ii) detecting by a sensor an amount of light collected by the camera; (iii) determining whether the amount of light collected by the camera is substantially equivalent to the predetermined amount of light; and (iv) closing the aperture after determining that the predetermined amount of light has been collected by the camera. In addition, the sensor may be sensitive or selectively sensitive to any range of wavelengths applicable for a particular application. Such a sensor may continuously measure the amount of light entering the aperture or may measure the amount of light collected through the aperture at a plurality of discrete time points after the opening of the aperture in order to take intermittent measurements of the collected amount of light. When the sensor has determined that the predetermined amount of light has been collected through the aperture, the sensor may be configured to close the aperture by way of a controller, a switch, a mechanical component, or another element of the camera.

In yet another embodiment, the aperture may be opened a plurality of times (i.e., to generate a plurality of images). This may be particularly desirable in cases where the camera lacks an auto exposure function or is otherwise unable to determine the period of time or aperture size required to collect the predetermined amount of light during a first opening of the aperture. In a particular embodiment, the camera may open its aperture to take a preliminary first image of the sample, and then use information about the first image to adjust the camera settings for a second or subsequent image. In such an embodiment, opening the aperture may include: opening the aperture for a period of time to collect an amount of light from the processed sample; measuring the amount of light collected from the processed sample; determining whether the amount of light collected from the processed sample is substantially equivalent to the predetermined amount of light; opening the aperture for a second period of time if the amount of light received from the sample is not substantially equivalent to the predetermined amount of light, wherein the second period of time is different than the first period of time; and correlating the second period of time that the aperture is open with the predetermined amount of light to obtain the concentration of an analyte or total protein in a sample. The second period of time may be determined based on an analysis of the amount of light collected from the sample during the first opening of the aperture. For example, the camera may use an algorithm that correlates a period of time that the aperture is open and an amount of light collected from the processed sample, and the method may further include determining, based on the first period of time and the first collected amount of light, a second period of time that would allow the camera to collect the predetermined amount of light from the sample.

In some embodiments, the camera may use an iterative approach to collect the predetermined amount of light. In such a case, the aperture may be opened a plurality of times, wherein each successive period of time is different from the previous period of time. The period of time that the aperture is open may iteratively increase or decrease by a predetermined amount of time (i.e., an iterative "step"). Additionally or alternatively, an algorithm may be used to determine the magnitude and/or direction of the iterative changes in the period of time the aperture is open. This may allow successive images taken by the camera to converge on the predetermined amount of light.

Additionally or alternatively, the camera may open the aperture a number of times for different periods of time, in order to take images at a range of exposure levels. The plurality of images produced by the camera may undergo post-processing to determine which image was produced with the predetermined amount of light. In such an embodiment, measuring the period of time that the aperture is open may include measuring the brightness, color, or another characteristic of a plurality of images, and selecting from the plurality of images an image which most closely equals the predetermined exposure level (e.g., the image produced via the collection of the predetermined amount of light). The period of time that the aperture is open associated with this image may then be used to correlate the shutter speed a concentration of an analyte or total protein in the sample.

The measured period of time may be used to quantify a concentration of an analyte or total protein in the processed sample. In some embodiments, the measured period of time may be displayed on a display or user interface of the camera. In other embodiments, the measured period of time and/or shutter speed may be transmitted to a computing device, a memory, a remote computer, a server, or another system for e.g., further analysis, processing, or correlation.

In some embodiments, the methods of the disclosure further include correlating the period of time that the aperture is open with the predetermined amount of light to obtain the concentration of an analyte or total protein in the sample. One such embodiment is illustrated in step 105 of the method 100 in FIG. 1. As described previously in relation to step 101, the sample may be contacted with a colorimetric reagent to obtain a processed sample, which may exhibit varying degrees of coloration depending on the concentration of a target analyte or total protein present in the sample. For example, shows three samples containing colorimetric reagents with no creatinine, and three processed samples containing colorimetric reagents and 2000 mg/dL of protein and 1000 mg/dL creatinine. Using the methods of the disclosure, the concentration of creatinine or total protein in the processed sample may be estimated by measuring a coloration, brightness, chromacity, intensity, opacity, or another optical property of the sample, for example, by taking an image of the processed sample.

In certain embodiments of the disclosure, if the optical properties of the produced images are predetermined (e.g., a uniform amount of light is collected to produce each image), measuring various camera settings that produce such image may allow a user to estimate the concentration of an analyte or total protein in a sample. For example, instead of using identical camera settings to take images of varying coloration, wherein the coloration of the images is indicative of the concentration of analyte or total protein in the sample, identical images may be taken of different samples, and the camera settings used to achieve the identical images may be indicative of the concentration of an analyte or total protein. In one example, the image exposure (i.e., the amount of light collected from the sample) may remain constant, while the shutter speed is measured. Measuring the period of time that the aperture is open as reflected by the shutter speed, can be used to determine the concentration of analyte or total protein in the processed sample.

Figure 3A:
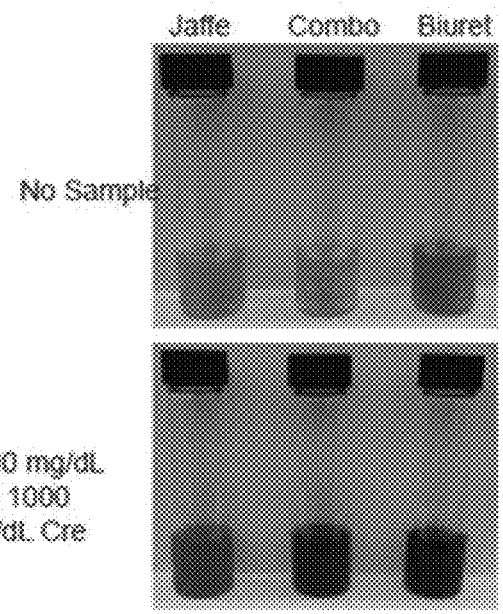
FIG. 3A is a photo of six sample aliquots prepared according to the method of the disclosure. The colorimetric technique used in sample preparation is noted above the sample aliquot. In the Figure, Pro=Total Protein and Cre=Creatinine.
Figure 3B:
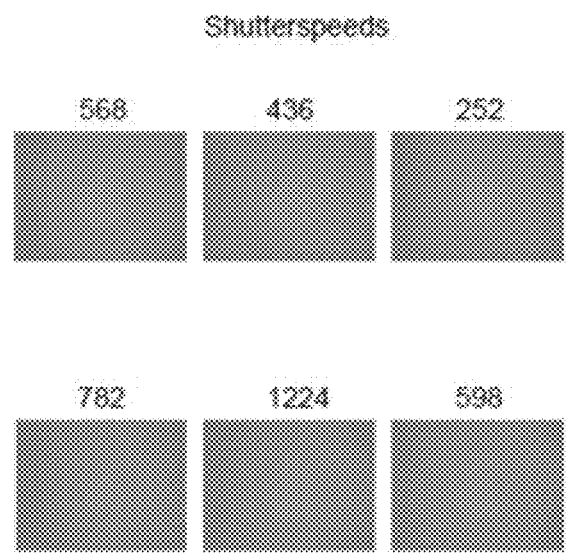
FIG. 3B is a series of experimental images generated by a camera according to a method of the disclosure. The shutter speed corresponding to each image is displayed above the image.

FIG. 3B shows the six images generated by collecting a predetermined amount of light from the six samples shown in FIG. 3A. Each image representing a sample of FIG. 3A is located in the corresponding location in FIG. 3B (i.e., the top left image in FIG. 3B corresponds to the top left sample in FIG. 3A, etc.) As shown in the figure, the six images produced by the camera appear substantially the same color, brightness, and/or exposure despite the coloration differences seen in the samples. This is due to the camera opening the aperture for different period of time for each image (568, 436, 252, 782, 1224, and 598 milliseconds as shown in the figure) in order to produce an image of identical color and/or exposure no matter the original sample color.

One of skill in the art will recognize that the period of time that the aperture is open will vary depending on characteristics of the camera and the processed sample to be imaged. For example, in certain embodiments of the method of the disclosure, the period of time may be in the range of about 0.1 ms to about 10 seconds, for example, between about 0.1 ms to about 5 s, or about 0.1 ms to about 1 s, or about 1 ms to about 10 s, or about 1 ms to about 5 s, or about 10 ms to about 10 s, or about 10 ms to about 5 s, or about 100 ms to about 10 s, or about 100 ms to about 1 s.

Figure 4A:
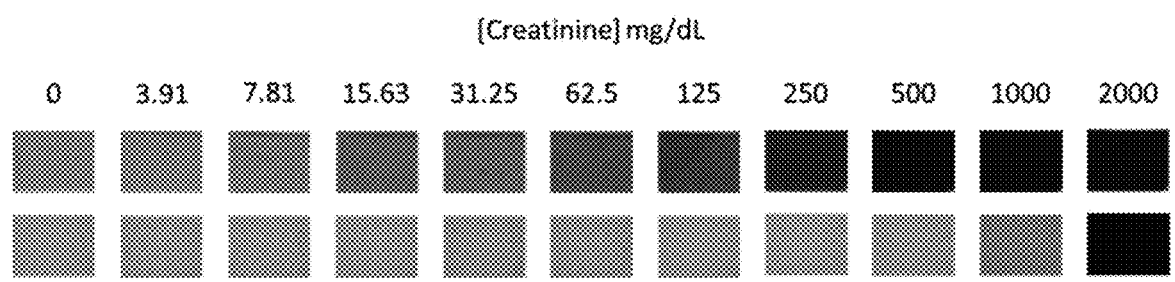
FIG. 4A shows photographs of a series of prepared samples according to a method of the disclosure.
Figure 4B:
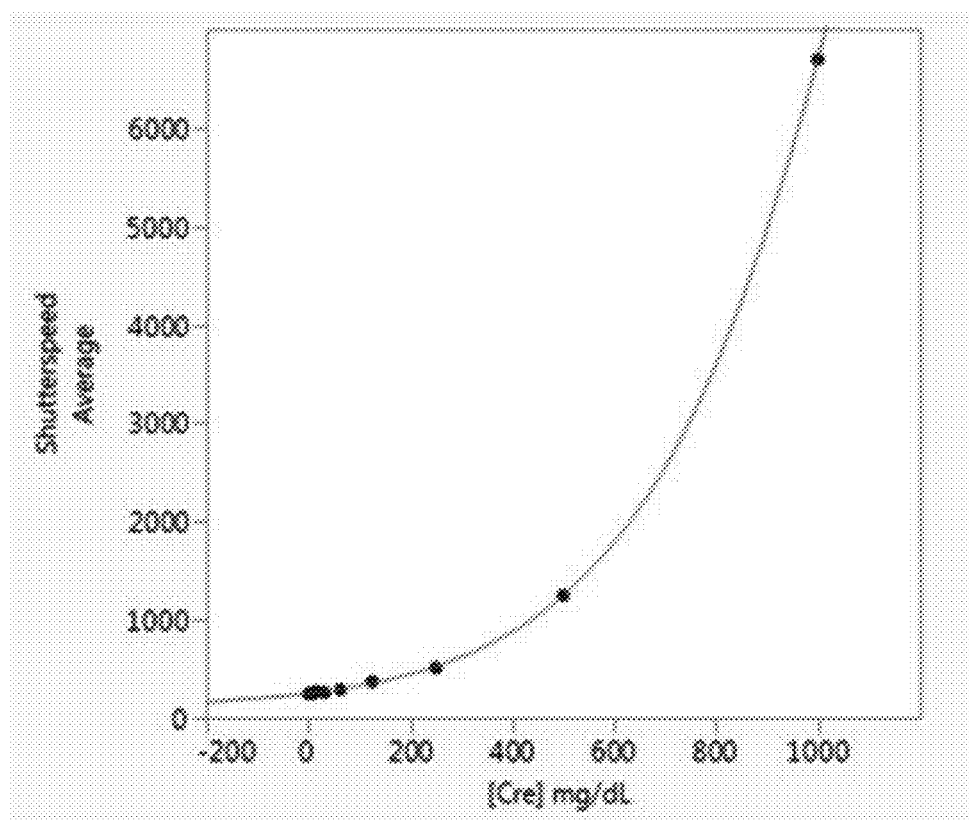
FIG. 4B is a correlation curve showing the relationship between the amount of creatinine in an experimental sample and the shutter speed measured according to a method of the disclosure.

FIG. 4A shows images of the samples generated by a camera for another series of processed samples including a colorimetric reagent and known amounts of creatinine ranging from 0 to 2000 mg/dL. Like the images in FIG. 3B, these images were taken by collecting a predetermined amount of light from the samples, thus producing images of substantially the same color and/or exposure. As apparent in the images, the samples containing more of the analyte (in this case, creatinine) are darker, therefore requiring the aperture to be opened for a longer period of time to collect the predetermined amount of light. The shutter speed measured by the camera can be correlated with an amount of creatinine in the sample, as illustrated in FIG. 4B, which is representative of a standard curve reflecting the relationship between the amount of an analyte in a sample and the shutter speed at which a camera collects a predetermined amount of light from a sample.

In some embodiments, correlating the period of time that the aperture is open with the predetermined amount of light may include conducting a regression analysis. In such embodiment, preliminary testing may be conducted and the experimental relationship between a known concentration of the analyte and the shutter speed, or the total protein and the shutter speed, may be plotted. A regression line may be used to estimate a regression function relating the two variables, such that subsequent experimental data may be interpreted based on the regression function. In such embodiment, correlating the period of time that the aperture is open with the predetermined amount of light to obtain the concentration of an analyte or total protein in the sample may include using a regression function to estimate the concentration of the analyte or total protein in the sample.

In other embodiments, a memory of a computing device, controller, processor, server, or another computing unit associated with the camera may include data relating a shutter speed with the predetermined amount of light to obtain the concentration of an analyte or total protein (e.g., a stored regression function). In such embodiments, correlating the period of time that the aperture is open with the predetermined amount of light may include determining the concentration of an analyte or total protein by way of a computing device. Such a determination may be made based on at least one of the species of analyte, the species of colorimetric reagent, and/or a measured period of time that the aperture is open. Such a determination may also be made based on the protein content, the species of colorimetric reagent, and/or a measured period of time that the aperture is open. Following determination of the concentration of the analyte or the total protein, the amount may be displayed on a display or user interface of the camera or a device associated with the camera. In other embodiments, the concentration of the analyte or the total protein may be transmitted to a computing device, processor, a memory of the camera, a memory of the computing device, or a remote computer, to a server or another system for further analysis, processing, or diagnosis.

As explained above in reference to the method 100 represented in Figure, in some embodiments the size of the aperture of the camera may be held constant and opening the aperture may include opening the aperture for a period of time sufficient to collect the predetermined amount of light. Measuring the concentration of an analyte or total protein in a prepared sample may then include measuring the period of time that the aperture is open to collect the predetermined amount of light. The measured period of time may then be correlated with the predetermined amount of light to obtain the concentration of an analyte total protein in the sample.

In another embodiment, the period of time that the aperture is open (i.e., the shutter speed) may remain constant. In such embodiment, the size of the aperture may be varied for each image, and the size of the aperture may be measured to determine the concentration of an analyte or total protein in the sample. For example, the period of time may range of about 0.1 ms to about 10 seconds, for example, between about 0.1 ms to about 5 s, or about 0.1 ms to about 1 s, or about 1 ms to about 10 s, or about 1 ms to about 5 s, or about 10 ms to about 10 s, or about 10 ms to about 5 s, or about 100 ms to about 10 s, or about 100 ms to about 1 s. In these embodiments, the predetermined amount of light when the numerical aperture is, for instance, between about 0.01 and about 0.99, between about 0.055 and 0.9, or between about 0.1 and 0.5.

Figure 5:
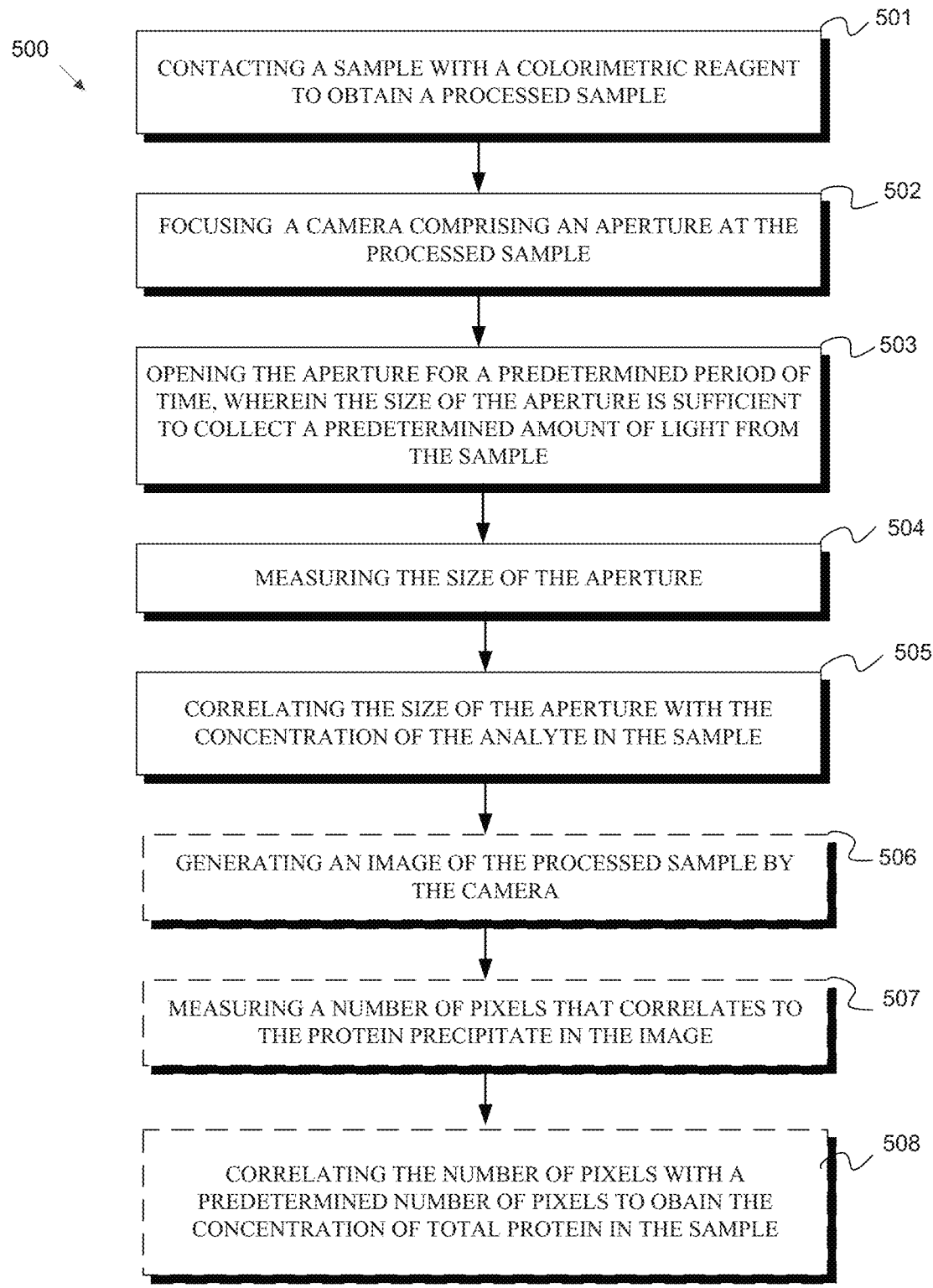
FIG. 5 is a flowchart of a method according to an embodiment of the disclosure.

FIG. 5 illustrates a flowchart of such a method 500 for measuring a concentration of an analyte and/or total protein concentration in a sample.

Steps 501 and 502 of method 500 may include steps similar to steps 101 and 102 of method 100, as described previously. In some embodiments, the contacting of the sample with a colorimetric reagent (101, 501) and focusing of the camera (102, 502) may be performed substantially the same as in method 100. Method 500 may further include opening the aperture for a discrete period of time, where the aperture size is related to the concentration of the analyte or total protein in the sample. For instance, step 503 includes opening the aperture for a predetermined period of time, wherein the size of the aperture is sufficient to collect a predetermined amount of light from the sample. The aperture size that allows the camera to collect the predetermined amount of light during the period of time that the aperture is open may then be measured as represented in step 504.

An optimal aperture size (i.e., an aperture size that allows the camera to collect the predetermined amount of light in the predetermined period of time) may be determined by an automatic exposure function, as described previously in relation to shutter speed. In such an embodiment, opening the aperture for a period of time may include using an automatic exposure function to open the aperture such that the size of the aperture is sufficient to collect a predetermined amount of light from the sample. Accordingly, measuring the size of the aperture may include determining the size of the aperture using the automatic exposure function. As described previously, such a determination may be based on the optical properties of the processed sample and/or at least one of the periods of time and the predetermined amount of light.

Additionally or alternatively, methods involving measuring the aperture size may include taking a plurality of images to collect the predetermined amount of light. In some embodiments, the camera may include a sensor, and the method may include: (i) opening the aperture to collect an amount of light from the sample, wherein the aperture includes a first aperture size; (ii) closing the aperture; (iii) measuring the amount of light collected from the processed sample by the sensor; (iv) determining whether the amount of light collected from the sample is substantially equivalent to the predetermined amount of light; (v) opening the aperture for a second period of time if the amount of light received from the sample is not substantially equivalent to the predetermined amount of light, wherein the aperture has a second aperture size, wherein the second aperture size is different than the first aperture size; and (vi) correlating the second aperture size of the aperture with the concentration of the analyte or total protein in the sample. Such an approach may use a first opening of the aperture to direct second or subsequent aperture openings, using an algorithm, an iterative approach, any of the methods described in relation to shutter speed, or some other process.

The method 500 may include correlating the size of the aperture with the concentration of the analyte or total protein in the sample as represented in step 505. Correlating the size of the aperture with the amount of the analyte or total protein may include comparing a measured aperture size with a standard curve to estimate the amount of the analyte or the total protein. Such a standard curve may be generated imaging a series of samples containing a known quantity of an analyte or total protein and plotting the measured aperture sizes of each sample relative to the known concentration. As described previously, a regression line may be used to estimate a regression function relating the two variables, such that subsequent experimental data may be interpreted based on the regression function relating e.g., the measured aperture size and the concentration of an analyte or total protein.

In some embodiments, the methods 100 and 500 may include determining a concentration of both the analyte and the total protein in the sample. The amount of total protein in the sample may be estimated through an analysis of an image of the sample, e.g., an image generated when light is collected by the camera for measurement of the concentration of an analyte. This process may include generating an image of the processed sample by the camera (steps 106 and 506); measuring a number of pixels that correlates to the protein precipitate in the image (steps 107 and 507); and correlating the number of pixels with a standard curve to obtain the concentration of total protein in the sample (steps 108 and 508).

In one embodiment, measuring the amount of a protein precipitate includes conducting a visual analysis of an image of the processed sample generated by the camera. An image of the processed sample may be generated during previous steps of the method, for instance, when the aperture of the camera is opened to collect the previously determined amount of light. The image may be generated by collecting light and recording it as an image using a light sensor of the camera, as described previously.

Figure 6A:
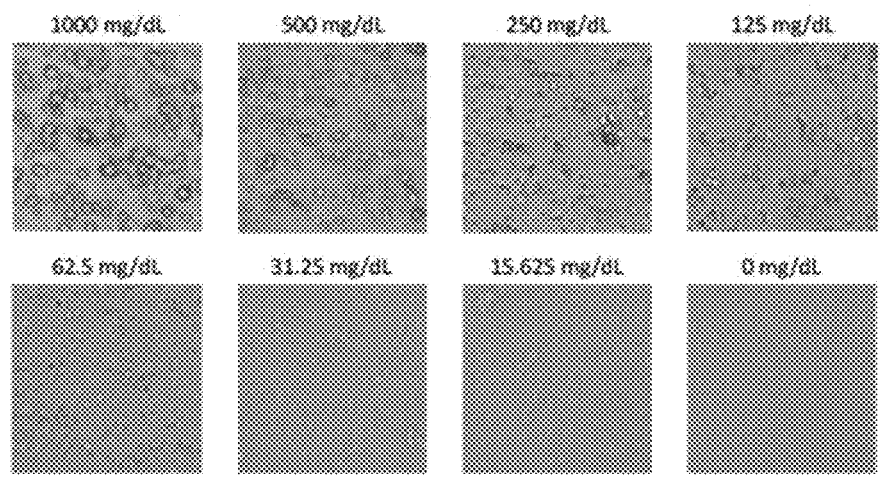
FIG. 6A is a series of experimental images generated by a camera according to a method of the disclosure and show an amount of precipitated protein in the prepared samples.

An image of the protein precipitate may include globules of precipitated protein that may appear in varying amounts in an image depending on the concentration of protein in the sample. FIG. 6A shows experimental images of processed samples containing between 0-1000 mg/dL of protein. As seen in FIG. 6A, the proteins may be visible by the naked eye, and appear as interruptions in an image of otherwise uniform exposure or coloration. In some embodiments, the images of the protein precipitate, such as the images seen in FIG. 6A, may be the same images used to measure the concentration of the analyte (i.e., the images produced when collecting the predetermined amount of light from the sample.) Additionally or alternatively, separate images may be generated for protein quantification, and the method may include opening the aperture to collect a second amount of light from the processed sample and/or generating an image of the processed sample.

The method may include processing the images of the protein precipitate. In some embodiments, images of the protein precipitate may undergo post-processing to increase clarity of the images, increase contrast, increase focus, or facilitate quantification of the proteins. For instance, the camera may be coupled to or communicates with a computing device, which includes a controller, processor, memory, or other components. Post-processing may include using an image processing program on a computing device, or executing instructions stored in a memory of the computing device. Additionally or alternatively, aspects of the image may be adjusted manually by a user of the camera by interacting with a user interface of the camera or associated computing device.

In some cases, a visual analysis may be used to quantify the amount of protein precipitate in a sample. In one embodiment, the method may include conducting a naked-eye analysis of an image produced by the camera to measure the concentration of protein precipitate in the sample. For instance, a user of the method may look at the image and count globules of precipitated protein, estimate an area of the image that includes protein precipitate, or conduct some other naked-eye analysis.

In some embodiments, an algorithm, program, or software may be used to quantify the protein precipitate in the processed sample. In some embodiments, a computing device coupled to or in communication with the camera executes instructions (e.g., instructions stored in a memory of the computing device) in order to measure an amount of protein precipitate in the processed sample. Such instructions may be executed by a processor of the computing device in order to automate a portion of the measurement described above in relation to naked-eye techniques. For example, the instructions may be configured to measure the amount of protein precipitate in the processed sample by measuring or determining a number of pixels that correlates to the protein precipitate (e.g., corresponds to protein precipitate globules or an area of the image that consists of a protein precipitate) in an image of the processed sample. Additionally or alternatively, the instructions may cause the computing device to measure an amount of a protein precipitate in the processed sample by measuring an area of an image of the processed sample that includes protein precipitate. Measuring the area that includes the protein precipitate may include determining a number of pixels of an image that relate to the protein precipitate. Differentiating the protein precipitate from the background of the image may include analyzing a numerical value associated with the pixels. For example, each pixel in an image may include a value corresponding to an amount of collected light, a level of intensity, brightness, coloration, greyscale, or another optical property of the pixel (e.g., a pixel in 8-bit image may be represented by a number between 0 and 255, where 0 corresponds to black and 0 corresponds to white). In a particular example, a threshold value may be set such that pixels with a value higher than the threshold are considered as comprising the protein precipitate, while those with a value lower than the threshold value are considered background. In such a case, determining a number of pixels that relate to the protein precipitate may include determining a number of pixels that are above or below some threshold value.

Additionally or alternatively, the precipitated protein may be measured by determining a homogeneity of the produced image. A more heterogeneous (i.e., less homogenous) image may represent a greater amount of precipitated protein, while a homogenous image may indicate a lesser amount of protein. In such an example, the homogeneity of an image may be determined by analyzing numerical values (e.g., values associated with the collected light, as described previously) associated with each pixel in the image. In a particular example, determining the homogeneity of the image may include calculating a standard deviation of the values associated with each pixel in the image, where a higher standard deviation may be the result of a higher amount of precipitated protein (and vice versa)

Figure 6B:
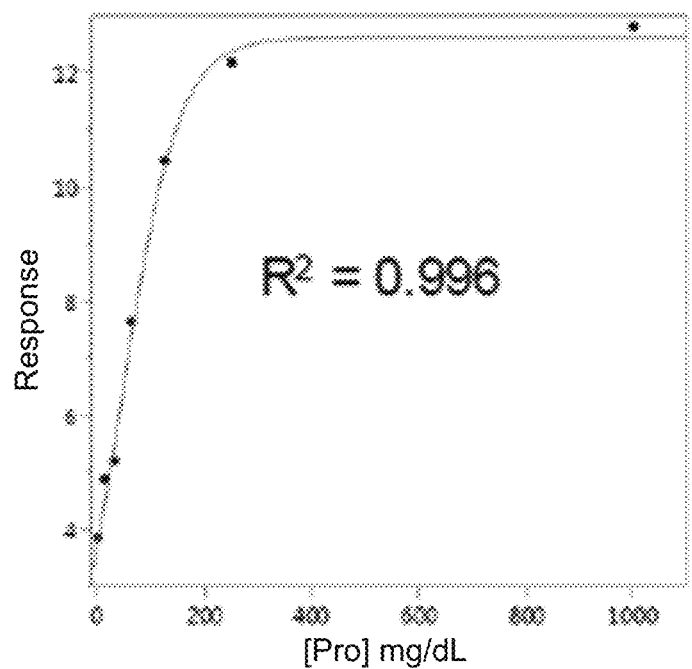
FIG. 6B is a correlation curve showing the relationship between the amount of protein in an experimental sample and the measured protein precipitate according to a method of the disclosure.

FIG. 6B shows a plot of the relationship between the concentration of protein in a sample and the measured amount of protein precipitate in an image of the processed sample. The "response", as referenced in FIG. 6B, relates to the homogeneity of the image, as determined by the process described previously. The amount of protein precipitate in the processed sample was determined using an image analysis software that calculates the homogeneity of an image (i.e., the response) and correlates the homogeneity to an amount of protein in the imaged sample. In some cases, correlating the amount of a protein precipitate in the processed sample to the concentration of protein in the sample may include conducting a regression analysis. In such a case, preliminary testing may be conducted and the experimental relationship between a known concentration of the protein and the precipitate in an image of the sample may be plotted. A regression line may be used to estimate a regression function relating the two variables, such that subsequent experimental data may be interpreted based on the regression function. In such embodiment, correlating the amount of protein precipitate in the processed sample to the amount of protein in the sample may include using a regression function to estimate the amount of protein in the sample.

Figure 11A:
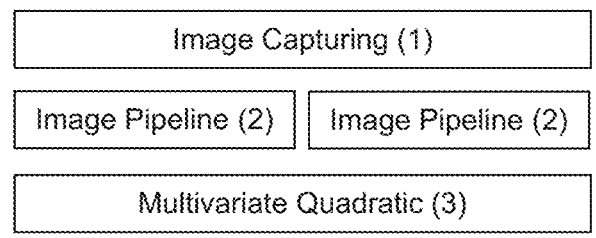
FIG. 11A is a diagram of determining the amount protein in the sample using multivariate quadratic equation according to an embodiment of the disclosure.
Figure 11B:
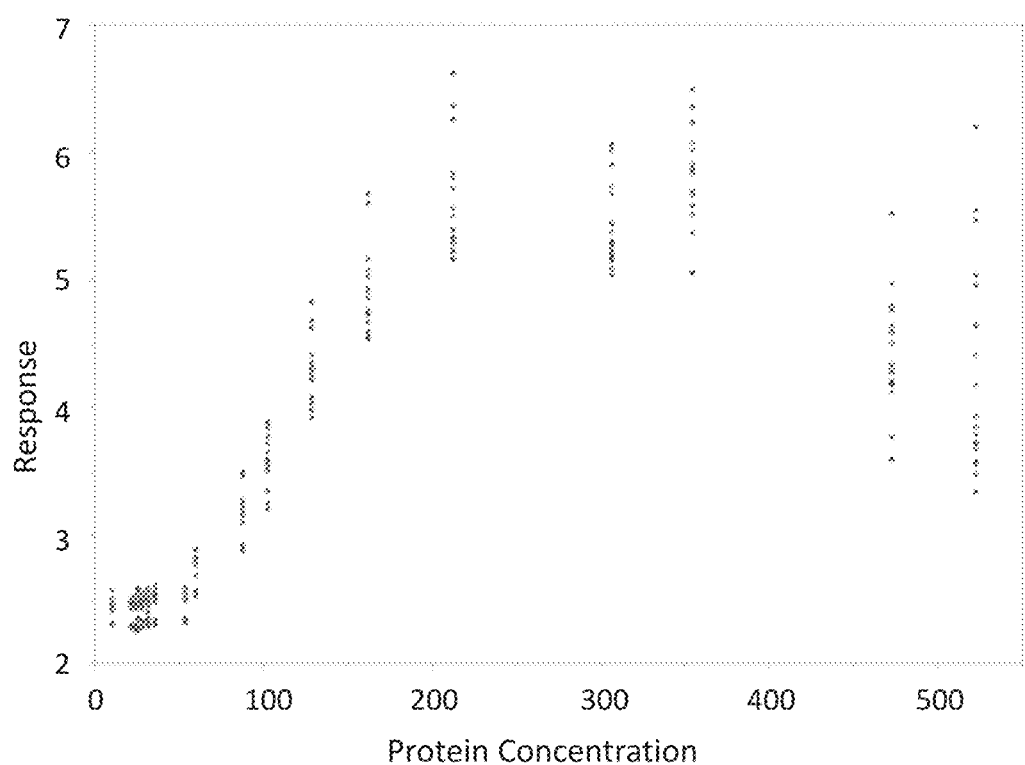
FIG. 11B is a plot of the relationship between the amount of protein in the sample and a sliding window standard deviation image feature on multiple devices.
Figure 11C:
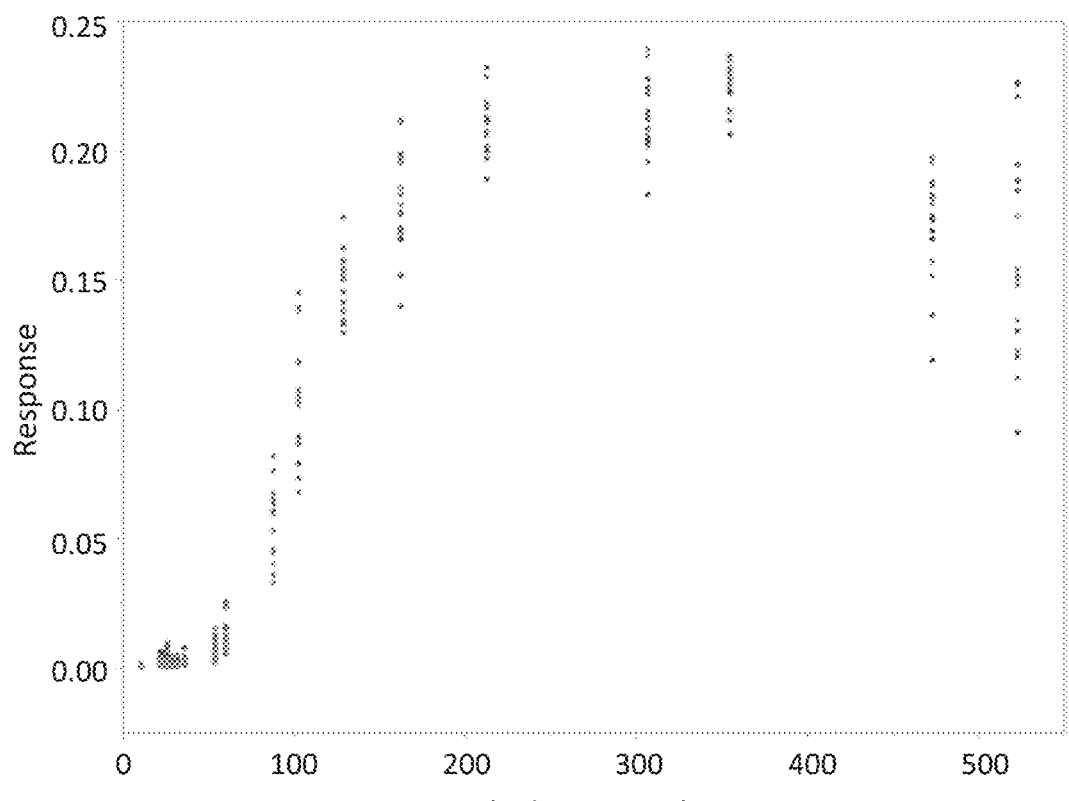
FIG. 11C is a plot of the relationship between the amount of protein in a sample and an average contour area image feature on multiple devices.
Figure 11D:
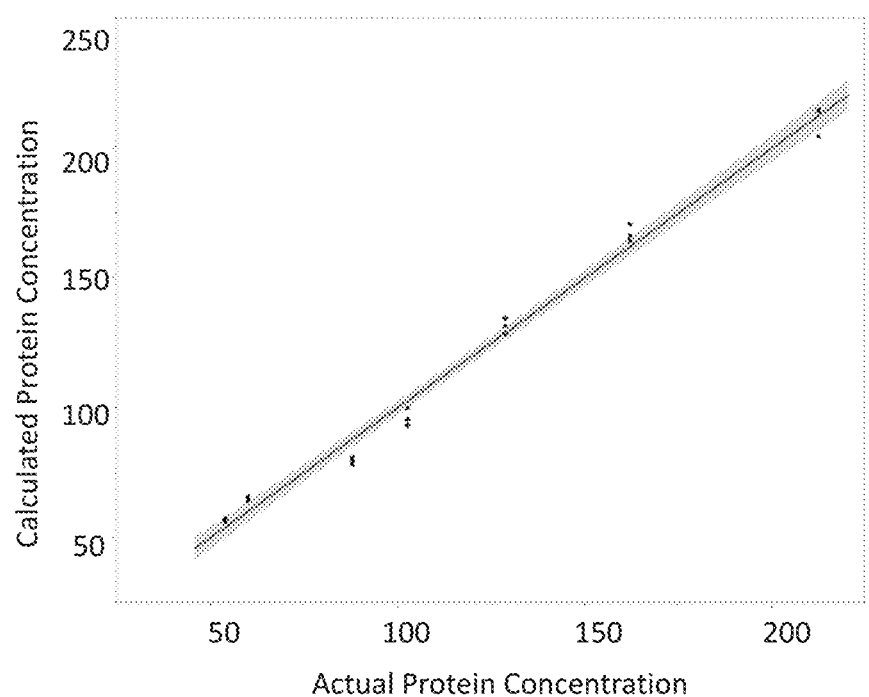
FIG. 11D is a linearity plot of a multivariate quadratic regression according to an embodiment of the disclosure using two image features on a single device.

In some embodiment of the disclosure, correlating the amount of protein precipitate in the processed sample to the amount of protein in the sample uses multivariate quadratic equation as provided in FIG. 11A. Multiple images of the protein precipitate are obtained from different locations within the sample in step 1. Then at step 2, the images are processed through a multitude of image processing pipelines that extract features of the protein precipitate within the images. In certain embodiments, the image processing pipelines may include sensor noise correction, contrast and edge enhancements, edge and contour detection, contour area, the Fourier transform, and/or the standard deviation. The features extracted through the image processing pipelines are correlated to protein in step 3 using a multivariate quadratic equation as follows:

$$[\text{PRO}] = c_1 x_1^2 + c_2 x_1 + c_3 x_2^2 + c_4 x_2 + \ldots + c_a x_n^2 + c_b x_n + c_0$$

where $x_1$ is an image feature 1; $x_2$ is an image feature 2; $x_n$ is an image feature n. FIG. 11B shows a plot of the relationship between the concentration of protein in the sample on multiple devices and a sliding window standard deviation image feature; and FIG. 11C shows a plot of the relationship between the concentration of protein in a sample on multiple devices and the average contour area image feature. FIG. 11D shows a linearity plot for a single device after performing a multivariate quadratic regression on the two image features.

Figure 12A:
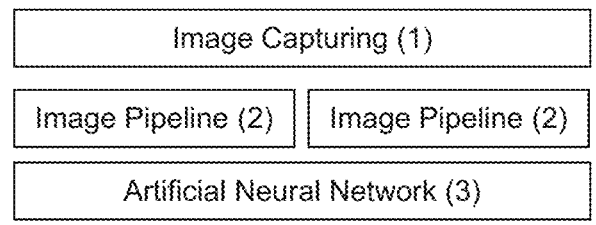
FIG. 12A is a diagram of determining the amount protein in the sample using artificial neural network according to an embodiment of the disclosure.
Figure 12B:
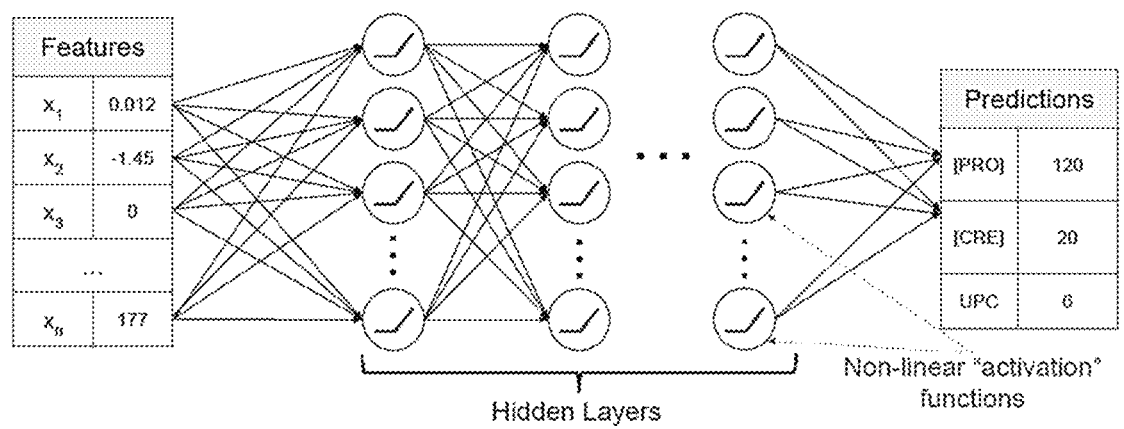
FIG. 12B is a diagram of the structure of artificial neural network. $x_1$ is an image feature 1, $x_2$ is an image feature 2, and $x_n$ is an image feature n.
Figure 12C:
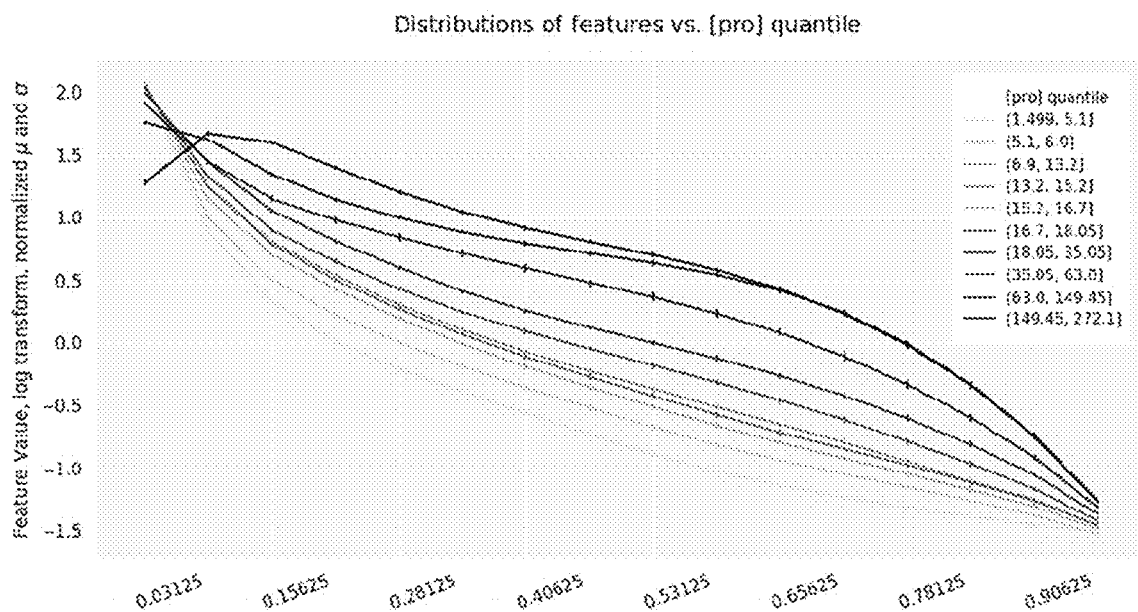
FIG. 12C is a plot of the relationship between the amount of protein in a sample and a histogram sliding window standard deviation image feature on multiple devices.
Figure 12D:
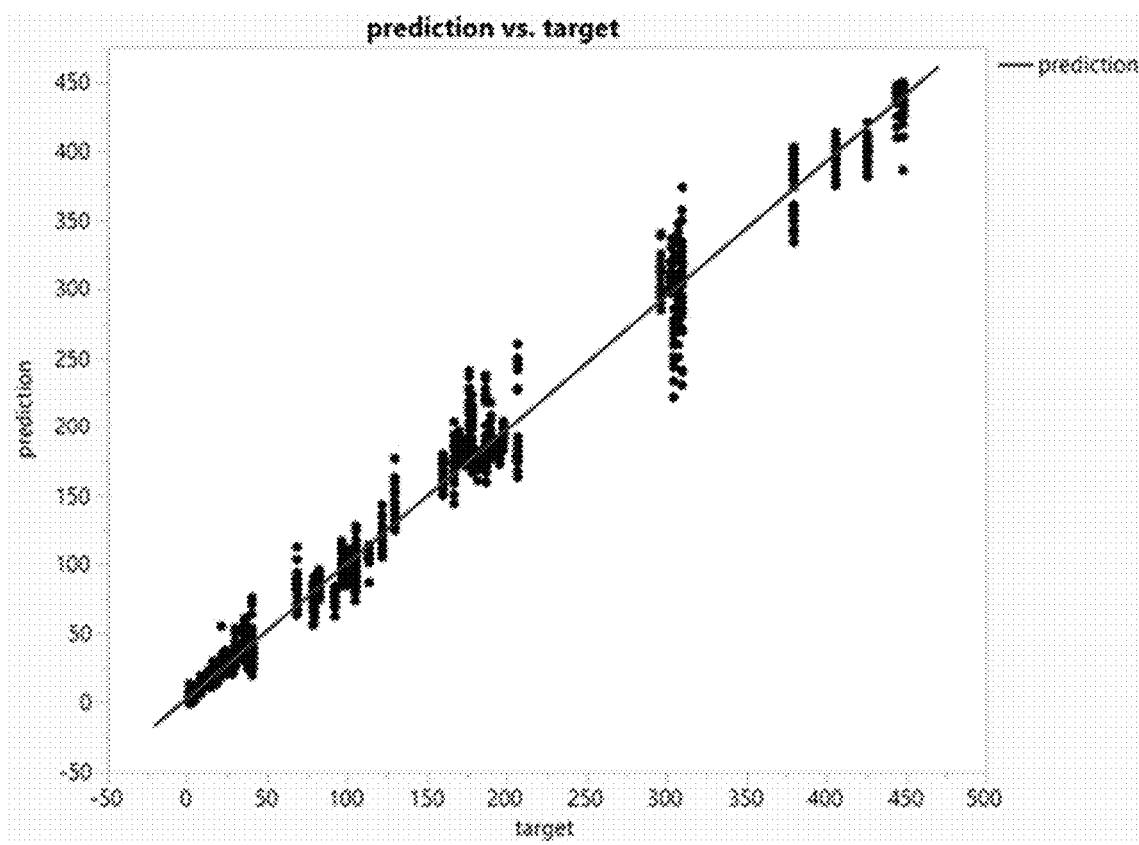
FIG. 12D is a linearity plot of a training of neural network according to an embodiment of the disclosure using an image feature on multiple devices.

In some embodiment of the disclosure, correlating the amount of protein precipitate in the processed sample to the amount of protein in the sample uses artificial neural network as provided in FIG. 12A. Multiple images of the protein precipitate are obtained from different locations within the sample in step 1. Then at step 2, the images are processed through a multitude of image processing pipelines that extract features of the protein precipitate within the images. In certain embodiments, the image processing pipelines may include sensor noise correction, contrast enhancements, and/or histograms of the Fourier transform and/or the standard deviation. The features extracted through the image processing pipelines are correlated to protein in step 3 using artificial neural network. The structure of artificial neural network is provided in FIG. 12B (where $x_1$ is an image feature 1, $x_2$ is an image feature 2, $x_n$ is an image feature n). FIG. 12C shows a plot of the relationship between the concentration of protein in a sample on multiple devices and a histogram sliding window standard deviation image feature; and FIG. 12D shows a linearity plot for multiple devices after training the neural network on the image feature.

In other cases, a computing device, controller, processor, server, or another computing unit associated with the camera may include data relating the concentration of a protein precipitate in the processed sample with the amount of protein in a sample. In such an embodiment, correlating the amount of protein precipitate in an image with the amount of protein in the sample may include determining the amount of protein by way of a computing device. Such a determination may be made based on at least one of the number of a number of pixels that correlates to the protein precipitate counted in the image, the measured area consisting of precipitated protein in the image. Following determination of the concentration of the protein, the methods 100 and 500 may include displaying the concentration on a display or user interface of the camera or a device associated with the camera. In other embodiments, the concentration of the protein may be transmitted to a computing device, processor, a memory of the camera, or a remote computer, to a server or another system for e.g., further analysis, processing, or diagnosis.

In some embodiments, the methods 100 and 500 further include making a determination about a health state of the user based on at least the determined concentration of an analyte and/or protein in the sample. In some cases, a computing device (e.g., a computer, a server, a processor, or a controller) in communication with the camera may use the determined concentration of analyte and/or protein to determine a health state, diagnose a disease, express a risk factor, or offer some other information about the health of a patient. In one embodiment, a relationship (e.g., a ratio) of the amount of protein and analyte may be indicative of a health state, and determining the health state may include determining whether the relationship of the analyte and creatinine is higher or lower than a threshold level. In a particular embodiment, the analyte may be creatinine, and the methods 100 and 500 may include determining a urine protein: creatinine ratio ("UPC ratio") of the sample. In such a case, diagnosing a health state (e.g., proteinuria) may include determining whether the UPC ratio is above or below a threshold value. Other health states and analyses are envisioned by one of ordinary skill in the art.

The example methods 100 and 500 illustrated in FIGS. 1 and 6 are meant as illustrative, non-limiting examples. Steps and steps described herein may be carried out sequentially or in parallel. Furthermore, the various step and steps may be carried out in a different order than described herein and some steps and steps may be omitted, skipped, and/or repeated. Additional or alternative elements of the methods and additional or alternative components of the systems are anticipated, as will be obvious to one skilled in the art.

Figure 7:
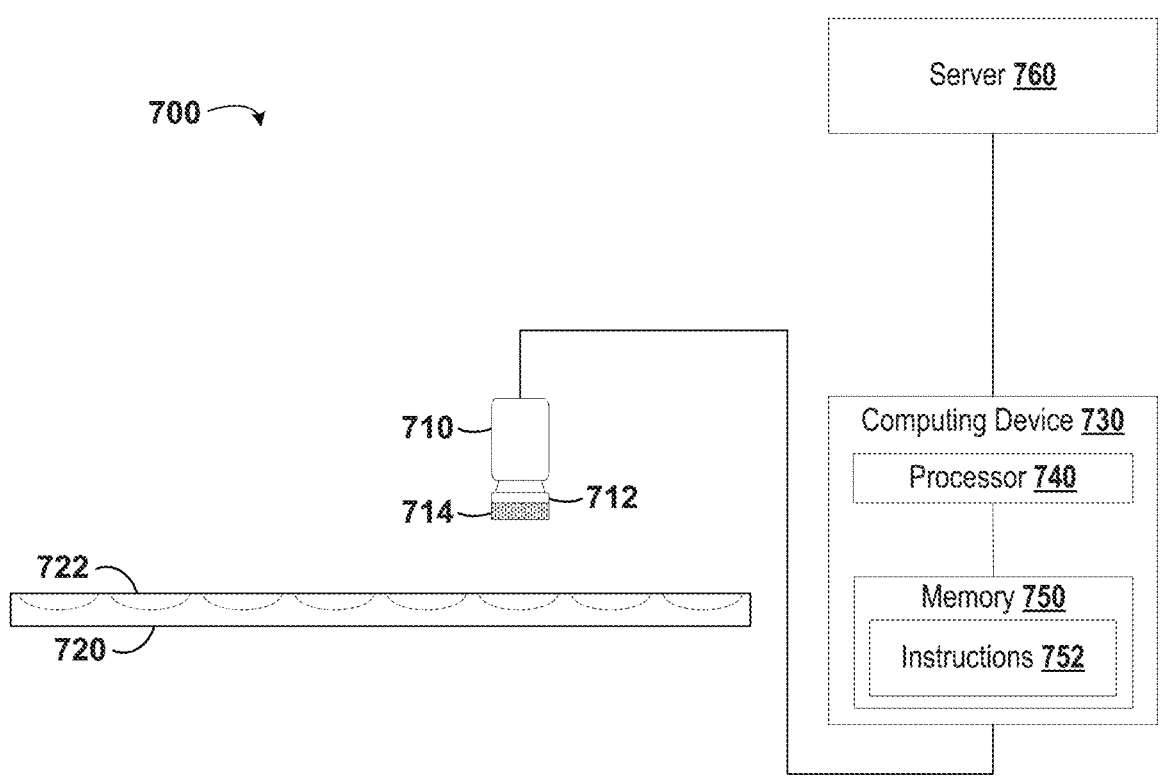
FIG. 7 is a diagram showing a camera and a prepared sample according to an embodiment of the disclosure.

FIG. 7 is an illustration of a system 700, for example a system used in either of the methods 100 or 500, according to example embodiments of the disclosure. The system 700 may include a camera 710, a multi-well sample plate 720, a computing device 730 (including a processor 740 and a memory 750), and a server 760. The multi-well plate 720 may include multiple wells 722.

The camera 710 may include one or more light sensors, such as a charge-coupled device (CCD), an active pixel sensor (APS), a complementary metal-oxide semiconductor (CMOS), a FOVEON X3® sensor, or another sensor. Such a light sensor may be sensitive to any range of wavelengths of interest for a given application, as understood by a person of ordinary skill in the art. In one embodiment, the light sensor may be sensitive to a range of wavelengths corresponding to the visual spectrum or a portion of the visual spectrum (i.e., wavelengths between about 190 nm to 700 nm). Additionally or alternatively, the light sensor may be sensitive or selectively sensitive to wavelengths in an infrared and/or ultraviolet range. In one embodiment, the light sensor may be selectively sensitive to a range of wavelengths corresponding to the wavelengths reflected, emitted, or transmitted from the prepared sample, e.g., wavelengths corresponding to the color of the prepared sample after it reacts with a colorimetric reagent, wavelengths corresponding to the emission spectrum of a fluorophore, or another range of wavelengths. Such a light sensor may also be a black/white light sensor, such that substantially all incoming light is detected and recorded the same in the range to which the sensor is sensitive, regardless of wavelength.

The camera 710 may also include an aperture 712 and one or more optical filters 714. The optical filter may only pass light through to the aperture 712 within a certain wavelength range. Such a filter 714 may be configured to selectively pass or block light of a certain wavelength or range of wavelengths such that only light of a particular wavelength or range of wavelengths is collected by the camera 710. For instance, the range of wavelengths passed by the filter 714 may be related to the reflectance, emission, or transmittance spectrum of the processed sample. This range of wavelengths may correspond to the color of a colorimetric reagent or of a product produced by a reaction between the sample and a colorimetric reagent. In this way, only desired wavelengths may be recorded by the camera 710, thereby reducing noise or unnecessary image content. Additional or alternative uses for an optical filter 714 are also considered.

In another example embodiment, the analyte or total protein may be targeted by one or more fluorophores in a reagent. The fluorophores may emit light within a first specific wavelength range when excited by radiation within a second wavelength range. Thus, in such embodiments, the system 700 may additionally include an excitation source (e.g., a laser) that emits light within the second wavelength range to excite the fluorophores. In such a case, the filter may be configured to block all wavelengths outside of an emission spectrum of the processed sample.

As illustrated, the camera 710 is communicatively coupled to the computing device 730. Such a communicative coupling may be implemented using WiFi, over BLUETOOTH®, or via wireline interface (e.g., a USB cable), in various embodiments. Alternatively, in some embodiments, the camera 710 may be coupled to the computing device 730 over a wired connection, such as an Ethernet interface. In some embodiments, the camera 710 may be a camera attached to or integrated in a mobile computing device (e.g., a cellular phone). The mobile computing device may access the public Internet to transmit images (e.g., candidate images or target images of biological cells) to the computing device 730. In some embodiments, the camera 710 may additionally or alternatively be communicatively coupled to the server 760. For example, in some embodiments, the camera 710 may transmit images to the server 760, the server 760 may perform image processing or analysis (e.g., post-processing of the images, determinations about the concentration of an analyte or total protein in the sample), and the server 760 may then transmit the resulting information to the computing device 730.

The computing device 730, as illustrated, includes a processor 740 and a memory 750. The memory 750 includes instructions 752 stored thereon. The memory 750 may include volatile memory (e.g., RAM) and/or non-volatile memory (e.g., a hard drive). The memory 750 may also be internally communicatively coupled to the processor 740. The processor 740 may be configured to execute the instructions 752 stored in the memory 750 (e.g., to perform various computing tasks). Additionally or alternatively, the memory 750 may store images (e.g., recorded by the camera 710) and information relating to the images. The memory 750 may further store information relating to the measured concentration of analyte or protein in the sample.

The instructions 752 stored in a memory 750 of the computing device may include instructions relating to executing the methods described herein. For instance, the instructions 725 may instruct the camera to focus at the processed sample, open and/or close the aperture 712, generate an image of the sample (e.g., a sample located inside a well 722 of the multi-well plate), measure a period of time that the aperture 712 is open, and/or measure a size of the aperture. Such instructions 725 may also cause the computing device 730 to correlate a determined period of time and/or aperture size to a concentration of analyte or total protein in the sample. Additionally, the instructions 725 may relate to processing of an image produced by the camera 710. For example, the instructions 725 may cause the computing device 730 to process an image of the sample, measure the concentration of protein precipitate in the processed sample, and/or correlate the concentration of protein precipitate in the processed sample to the concentration of protein in the sample.

Example 1

Processed samples containing known quantities of glucose, albumin and alkaline phosphatase were imaged to have uniform brightness. The exposure time (i.e., the period of time that the aperture is open, shutter speed) of the images was plotted to show the relationship (i.e., a standard curve) between the exposure time and the amount of an analyte in the sample.

Images of a processed samples were taken by a PL-D725MU-T USB 3.0 camera (PixelLINK) with a CMOS light sensor and a monochromatic color space. The camera included an objective lens with a magnification of 10× and a numerical aperture of 0.28. The focal length of the objective lens was 20 mm, with a depth of focus of about 3.5 µm. A tube lens with a longer focal length was coupled to the objective lens in order to facilitate magnification and focusing of the camera. The tube lens had a focal length of 200 mm. An adapter was used to couple the len(s) to the camera at an optimal distance for focusing the image onto an image sensor of the camera.

Figure 8A:
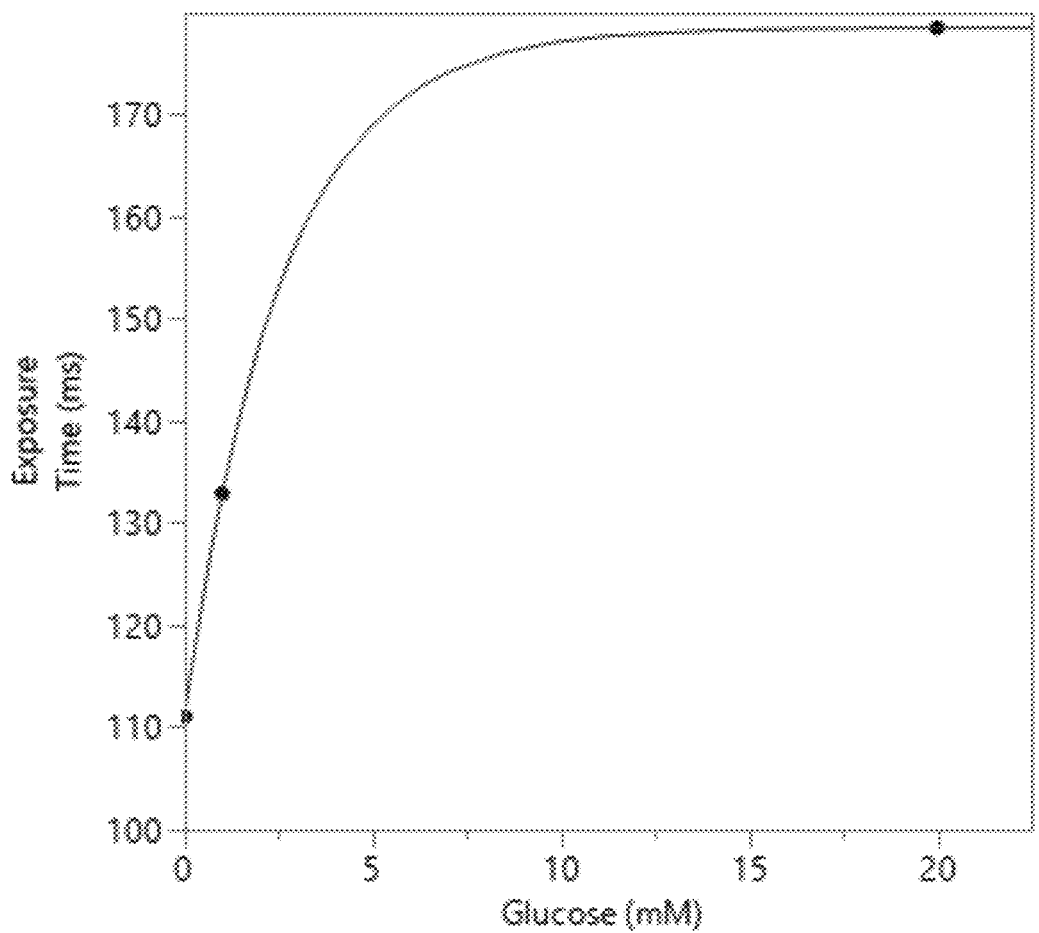
FIG. 8A is a correlation curve showing the relationship between the amount of glucose in an experimental sample and a period of time required to collect a predetermined amount of light from the sample.
Figure 8B:
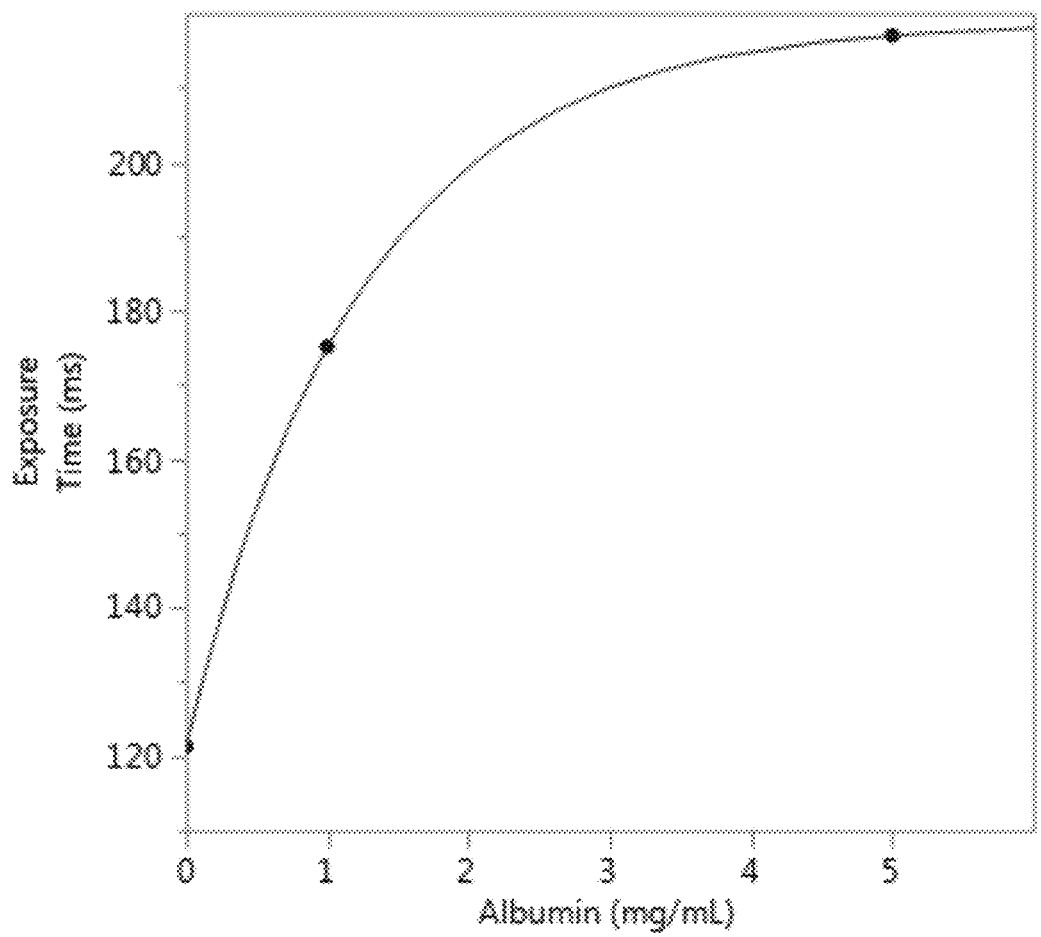
FIG. 8B is a correlation curve showing the relationship between the amount of albumin in an experimental sample and a period of time required to collect a predetermined amount of light from the sample.
Figure 8C:
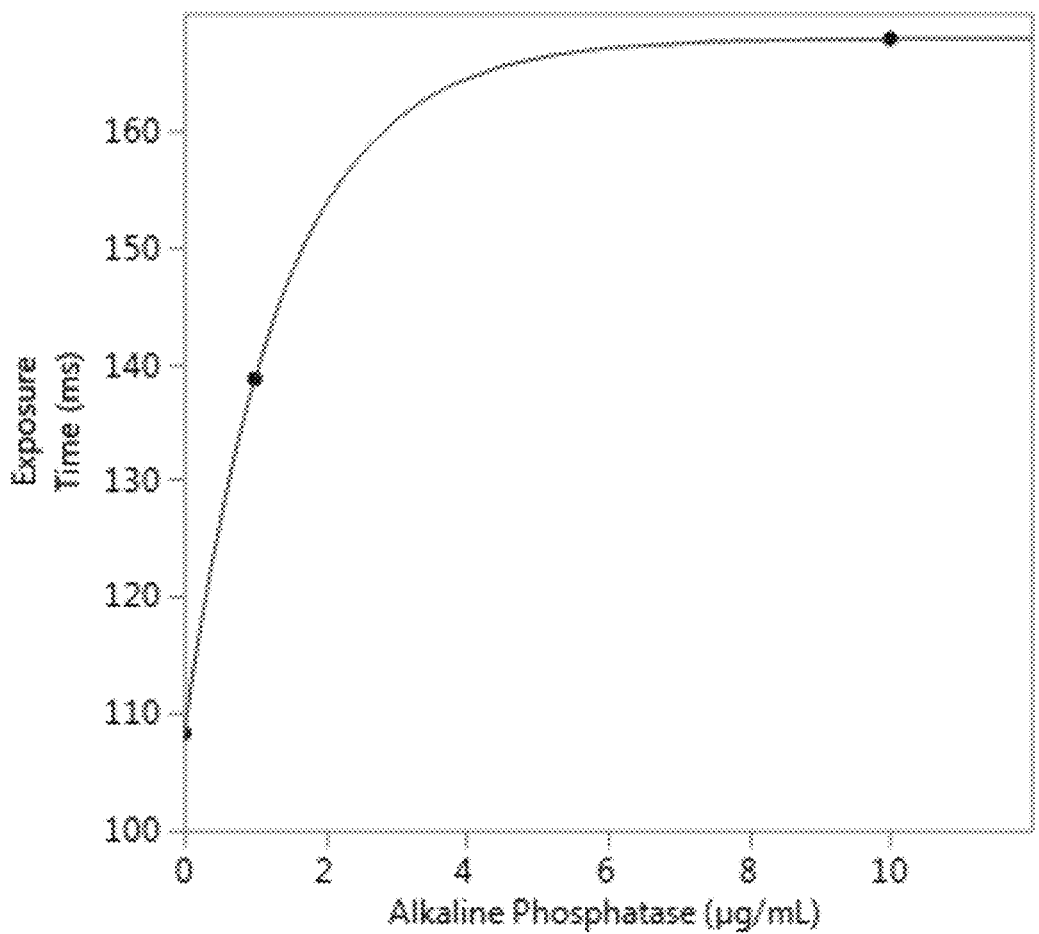
FIG. 8C is a correlation curve showing the relationship between the amount of alkaline phosphatase in an experimental sample and a period of time required to collect a predetermined amount of light from the sample.

Measurements taken according to the above described method are shown in FIGS. 8A-C. FIG. 8A illustrates a standard curve showing the relationship between the amount of glucose in an experimental sample and the predetermined period of time. This curve was obtained by preparing a negative control sample, 1 mM glucose sample, and 20 mM glucose sample. To fix the negative control sample, the following reagents were used: 590 µL of D.I. water, 10 µL of horseradish peroxidase (HRP), 10 µL glucose oxidase, 100 µL of 4-aminoantipyrine, and 100 µL of 1,7-dihydroxynapthalene in 95% ethanol. To fix the 1 mM glucose sample, the following reagents were used: 580 µL of D.I. water, 10 µL of horseradish peroxidase, 10 µL glucose oxidase, 100 µL of 4-aminoantipyrine, 100 µL of 1,7-dihydroxynapthalene in 95% ethanol, and 10 µL of glucose. To fix the 20 mM glucose sample, the following reagents were used: 380 µL of D.I. water, 10 µL of horseradish peroxidase, 10 µL glucose oxidase, 100 µL of 4-aminoantipyrine, 100 µL of 1,7-dihydroxynapthalene in 95% ethanol, and 200 µL of glucose. To each slide, 600 µL of sample (negative, 1 mM, and 20 mM) was added and imaged to obtain the curve illustrated in FIG. 8A.

FIG. 8B illustrates a correlation curve showing the relationship between the amount of albumin in an experimental sample and the predetermined period of time. This curve was obtained by preparing a negative control sample, 1 mg/mL albumin sample, and 5 mg/mL albumin sample. To fix the negative control sample, the following reagents were used: 880 µL of PBS buffer (pH 4.2) and 120 µL of bromocresol green (pH 4.2). To fix 1 mg/mL albumin sample, the following reagents were used: 870 µL of PBS buffer (pH 4.2), 120 µL of bromocresol green (pH 4.2), and 10 µL of albumin. To fix 5 mg/mL albumin sample, the following reagents were used: 830 µL of PBS buffer (pH 4.2), 120 µL of bromocresol green (pH 4.2), and 50 µL of albumin. To each slide, 600 µL of sample (negative, 1 mg/mL, and 5 mg/mL) was added and imaged to obtain the curve illustrated in FIG. 8B.

FIG. 8C illustrates a correlation curve showing the relationship between the amount of alkaline phosphatase in an experimental sample and the predetermined period of time. This curve was obtained by preparing a negative control sample, 1 µg/mL alkaline phosphatase sample, and 10 µg/mL alkaline phosphatase sample. To fix the negative control sample, the following reagents were used: 1 mL of BCIP/NBT substrate (5-bromo-4-chloro-3-indolyl phosphate/nitro blue tetrazolium) and 1 mL of 1 M HCl. To fix 1 µg/mL alkaline phosphatase sample, the following reagents were used: 990 µL of BCIP/NBT substrate, 10 µL of alkaline phosphatase, and 1 mL of 1 M HCl to stop the reaction. To fix 10 µg/mL alkaline phosphatase sample, the following reagents were used: 900 µL of BCIP/NBT substrate, 100 µL of alkaline phosphatase, and 1 mL of 1 M HCl to stop the reaction. To each slide, 600 µL of sample (negative, 1 µg/mL, and 10 µg/mL) was added and imaged to obtain the curve illustrated in FIG. 8C.

Example 2

165 µL of urine sample was added to 1485 µL of a solution of 3,5-dinitrobenzoylchloride in 300 mM of phosphate buffer (pH 12.4) to obtain the processed sample. Images of 165 µL of the processed sample were taken by the camera described in Example 1.

Figure 9:
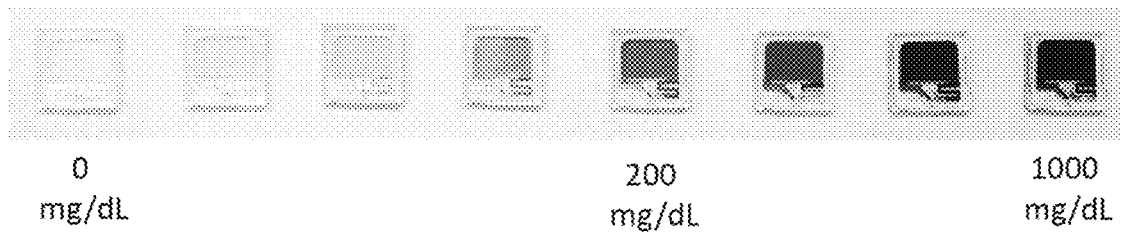
FIG. 9 provides images of samples having different creatinine concentrations that were processed according to methods of the disclosure.

FIG. 9 provides images of the samples generated by a camera showing an amount of creatinine, for example, ranging from 0 to 1000 mg/dL.

Figure 10:
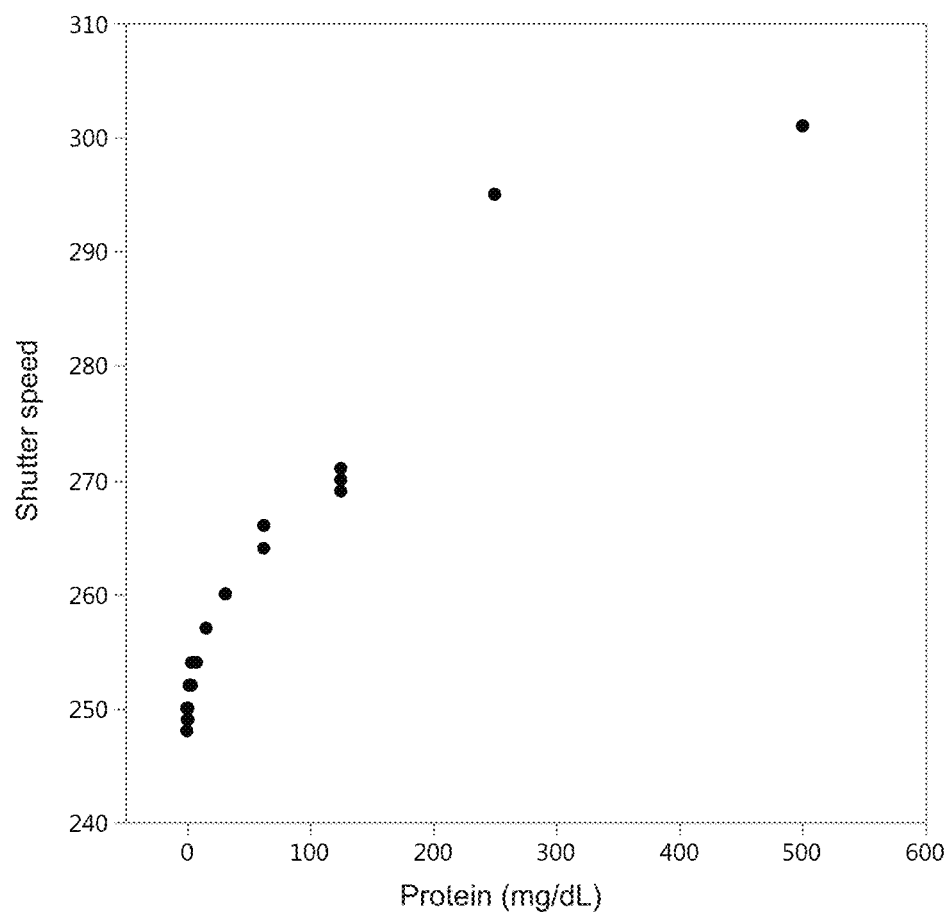
FIG. 10 is a graph showing a relationship between the amount of protein in an experimental sample and the shutter speed measured according to a method of the disclosure.

Another 165 µL of urine sample was added to 2475 µL of a solution of pyrocatechol violet reagent (0.28 mM pyrocatechol violet, 0.16 mM sodium molybdate, 120 mM succinic acid, and 1 mM sodium oxalate in deionized water) to obtain the processed sample. 165 µL of the processed sample was imaged as described above. The shutter speed of the processed sample is compared with a standard curve, which is obtained by plotting shutter speeds against known protein concentrations. Exemplary correlation of the relationship between the known amount of protein (for example, ranging from 0 to 500 mg/dL) and the shutter speed measured according to a method of the disclosure is provided in FIG. 10.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

The above detailed description describes various features and functions of the disclosed systems, devices, and methods with reference to the accompanying figures. While various aspects and embodiments have been disclosed herein, other aspects and embodiments will be apparent. The various aspects and embodiments disclosed herein are for purposes of illustration only and are not intended to be limiting, with the true scope being indicated by the following claims.

In the figures, similar symbols typically identify similar components, unless context dictates otherwise. The example embodiments described herein and in the figures are not meant to be limiting. Other embodiments can be used, and other changes can be made, without departing from the scope of the subject matter presented herein. It will be readily understood that the aspects of the disclosure, as generally described herein, and illustrated in the figures, can be arranged, substituted, combined, separated, and designed in a wide variety of different configurations, all of which are explicitly contemplated herein.

What is claimed is:

1. A method of measuring a concentration of an analyte or total protein in a biological sample, the method comprising:
    contacting the biological sample with a colorimetric reagent to obtain a processed sample;
    producing an image of the processed sample having a predetermined level of exposure by focusing a camera comprising an aperture at the processed sample; and opening the aperture for a period of time sufficient to collect a predetermined amount of light from the processed sample to produce the image;
    measuring the period of time that the aperture is open to collect the predetermined amount of light; and
    correlating the period of time with the concentration of the analyte or the total protein in the biological sample,
    wherein the predetermined amount of light is collected regardless of processed sample color.

2. The method of claim 1, wherein the analyte is selected from calcium ion, potassium ion, chloride ion, sodium ion, glucose, lactate, creatinine, creatine, urea, uric acid, ethanol, albumin, alkaline phosphatase, cholesterol, pyruvate, β-hydroxybutyrate, alanine aminotrasferase, aspartate aminotransferase, and cetylcholinesterase.

3. The method of claim 1, wherein the analyte is creatinine, glucose, albumin, or alkaline phosphatase.

4. The method of claim 1, wherein the colorimetric reagent is 2,4,6-trinitrophenol and a base; or the colorimetric reagent is methyl 3,5-dinitrobenzoate, 3,5-dinitrobenzoic acid, or 3,5-dinitrobenzoylchloride, and a base or a basic buffer; or the colorimetric reagent comprises 3,5-dinitrobenzoylchloride; or the colorimetric reagent is a reagent system comprising cupric ions, a hydroperoxide, and an oxidizable dye.

5. The method of claim 1, wherein the colorimetric reagent is one or more of glucose oxidase, hexokinase, alkaline copper tartarate, alkaline ferricyanide, and horseradish peroxidase.

6. The method of claim 1, wherein the colorimetric reagent is bromocresol green.

7. The method of claim 1, wherein the colorimetric reagent is a reagent system comprising 5-bromo-4-chloro-3-indolyl phosphate (BCIP) and nitro blue tetrazolium (NBT).

8. The method of claim 1, wherein the colorimetric reagent comprises pyrocatechol violet, benzethonium chloride, and pyrogallol red.

9. The method of claim 1, wherein the biological sample is a urine sample.

10. The method of claim 1, further comprising displaying the image of the processed sample on a user interface.

11. The method of claim 1, wherein the predetermined amount of light may be obtained by independently performing one, two, or three empirical experiments using a standard sample having a known concentration of the analyte.

12. The method of claim 1, wherein the predetermined amount of light is constant.

13. The method of claim 1, wherein the predetermined amount of light is selected by a user of the camera.

14. The method of claim 1, wherein the camera comprises a filter.

15. The method of claim 14, wherein the filter is configured to pass wavelengths corresponding to a wavelength range of the color resulting from the reaction between the colorimetric reagent and the processed sample.

16. The method of claim 1, wherein the camera comprises an automatic exposure function, and wherein measuring the period of time that the aperture is open comprises determining the period of time using the automatic exposure function.

17. The method of claim 16, wherein the determination is made based on at least one of the aperture size and the predetermined amount of light.

18. The method of claim 1, wherein the camera comprises a sensor, and wherein opening the aperture for a period of time sufficient to collect a predetermined amount of light from the processed sample comprises:
    opening the aperture;
    detecting by the sensor an amount of light collected by the camera;
    determining whether the amount of light collected by the camera is substantially equivalent to the predetermined amount of light; and
    closing the aperture after determining that the predetermined amount of light has been collected by the camera.

19. The method of claim 1, wherein the camera comprises a sensor, and wherein opening the aperture for a period of time sufficient to collect a predetermined amount of light from the processed sample comprises:
    opening the aperture for a period of time to collect an amount of light from the processed sample;
    closing the aperture;
    measuring the amount of light collected from the processed sample by the sensor;
    determining whether the amount of light collected from the processed sample is substantially equivalent to the predetermined amount of light;
    opening the aperture for a second period of time if the amount of light received from the processed sample is not substantially equivalent to the predetermined amount of light, wherein the second period of time is different than the first period of time; and
    correlating the second period of time that the aperture is open with the predetermined amount of light to obtain the concentration of the analyte or total protein in the processed sample.

20. The method of claim 1, wherein the analyte is creatinine.

21. The method of claim 20, further comprising determining a protein:creatinine ratio of the biological sample based on at least the concentration of creatinine in the processed sample and the concentration of total protein in the processed sample.

22. The method of claim 1, further comprising making a health determination based on at least the concentration of the analyte, total protein, or a combination thereof in the biological sample.

23. A method of measuring a concentration of an analyte and total protein in a biological sample, the method comprising:
contacting the biological sample with a colorimetric reagent and a protein precipitation reagent to obtain a processed sample comprising a protein precipitate;
determining the concentration of the analyte in the processed sample by producing a first image of the processed sample having a predetermined level of exposure by focusing a camera comprising an aperture at the processed; sample and opening the aperture for a period of time sufficient to collect a predetermined amount of light from the processed sample to produce the image, wherein the predetermined amount of light is collected regardless of processed sample color;
measuring the period of time that the aperture is open to collect the predetermined amount of light; and
correlating the period of time with the concentration of the analyte in the biological sample; and
determining the concentration of total protein by
generating a second image of the processed sample with the camera;
measuring a number of pixels that correlates to the protein precipitate in the image; and
correlating the number of pixels with a standard curve to obtain the concentration of total protein in the biological sample.

24. The method of claim 23, wherein the protein precipitation reagent is one or more water-miscible solvents (such as alcohol, e.g., isopropanol, methanol, or ethanol, ketone, e.g., acetone, methyl ethyl ketone, methyl isobutyl ketone, or cyclohexanone, tetrahydrofuran); or the protein precipitation reagent is a salt (such as ammonium sulfate or salts comprising polyvalent metallic ions); or the protein precipitation reagent is trichloroacetic acid, or trichloroacetic acid and acetone; or the protein precipitation reagent is a polymer (e.g., a non-ionic hydrophilic polymer, such as polyethylene glycols and dextrans).

25. The method of claim 23, wherein the protein precipitation reagent is an aqueous surfactant.

26. The method of claim 25, wherein the aqueous surfactant is benzalkonium chloride or benzethonium chloride.

27. The method of claim 23, wherein the second image of the processed sample is generated using the predetermined amount of light collected from the processed sample.

28. The method of claim 27, wherein the processed sample is imaged from a slide comprising the processed sample.

29. The method of claim 27, wherein the image is a black and white image.

30. The method of claim 23, wherein the predetermined amount of light is sufficient to measure an amount of the protein precipitate from an image of the processed sample.

* * * * *